(12) United States Patent
Scalise et al.

(10) Patent No.: US 12,226,339 B2
(45) Date of Patent: Feb. 18, 2025

(54) OSTOMY COLLECTION AND DRAINAGE SYSTEM

(71) Applicant: Hollister Incorporated, Libertyville, IL (US)

(72) Inventors: Anthony Scalise, Plainfield, IL (US); Jan Torstensen, Virum (DK); Christina Augustyn, Chicago, IL (US); Peter L. Visconti, Gurnee, IL (US); Patrick C. Tetzlaff, Caledonia, WI (US); Brian T. Leadingham, Pleasant Prairie, WI (US)

(73) Assignee: HOLLISTER INCORPORATED, Libertyville, IL (US)

( * ) Notice: Subject to any disclaimer, the term of this patent is extended or adjusted under 35 U.S.C. 154(b) by 0 days.

(21) Appl. No.: 18/594,890

(22) Filed: Mar. 4, 2024

(65) Prior Publication Data

US 2024/0207083 A1 Jun. 27, 2024

Related U.S. Application Data

(63) Continuation of application No. 16/980,264, filed as application No. PCT/US2019/025147 on Apr. 1, 2019, now Pat. No. 11,957,615.

(Continued)

(51) Int. Cl.
*A61F 5/448* (2006.01)
*A61F 5/44* (2006.01)

(52) U.S. Cl.
CPC ............ *A61F 5/448* (2013.01); *A61F 5/4407* (2013.01); *A61F 2005/4486* (2013.01)

(58) Field of Classification Search
CPC ....... A61F 5/445; A61F 5/4406; A61F 5/4404
See application file for complete search history.

(56) References Cited

U.S. PATENT DOCUMENTS 3,415,299 A * 12/1968 Hinman, Jr. .............. A61F 5/44
604/326
3,823,716 A * 7/1974 Hale ........................ A61F 5/44
604/335

(Continued)

FOREIGN PATENT DOCUMENTS

GB 2125130 A 2/1984
JP 2013543788 A 12/2013

OTHER PUBLICATIONS

International Search Report issued by ISA/EPO in connection with PCT/US2019/025147 dated Sep. 24, 2019.

(Continued)

*Primary Examiner* — Guy K Townsend
(74) *Attorney, Agent, or Firm* — Klintworth & Rozenblat IP LLP

(57) ABSTRACT

An ostomy collection and drainage system includes an ostomy pouch having an outer wall defining an internal collection area, an inlet opening formed in the outer wall and an outlet body connected to the outer wall having an outlet opening extending therethrough, the outlet body having one of a latch and a catch. The system further includes a closure configured for removable coupling to the outlet body and an adapter configured for removable coupling to the outlet body, the adapter having an adapter opening extending therethrough and the other of the latch and the catch. The adapter and the closure are interchangeably coupled to the outlet body such that in a first condition the adapter is coupled to the outlet body by way of engagement of the catch and the latch, and in a second condition the closure is coupled to the outlet body.

5 Claims, 12 Drawing Sheets

Related U.S. Application Data

(60) Provisional application No. 62/673,108, filed on May 17, 2018.

(56) References Cited

U.S. PATENT DOCUMENTS

| | | | | |
|---|---|---|---|---|
| 4,084,590 A * | 4/1978 | Caraway | ........ | A61F 5/445 604/350 |
| 4,238,059 A * | 12/1980 | Caraway | ........ | A61F 5/4405 285/332 |
| 4,254,771 A * | 3/1981 | Vidal | ........ | A61F 5/441 604/325 |
| 4,280,498 A * | 7/1981 | Jensen | ........ | A61F 5/4405 604/323 |
| 4,300,560 A * | 11/1981 | Steer | ........ | A61F 5/445 222/530 |
| 4,540,156 A * | 9/1985 | Cross | ........ | F16K 31/602 604/350 |
| 4,573,983 A * | 3/1986 | Annis | ........ | A61F 5/441 600/580 |
| 4,592,750 A * | 6/1986 | Kay | ........ | A61F 5/4407 604/277 |
| 4,634,437 A * | 1/1987 | Lowthian | ........ | A61F 5/44 600/580 |
| D300,361 S * | 3/1989 | Tokarz | ........ | D24/129 |
| 4,909,478 A * | 3/1990 | Steer | ........ | F16K 5/0414 604/323 |
| 5,098,420 A * | 3/1992 | Iacone | ........ | A61F 5/448 604/338 |
| 5,299,777 A * | 4/1994 | Milstead | ........ | F01M 11/0408 251/291 |
| 6,132,408 A * | 10/2000 | Lutz | ........ | A61F 5/4407 604/335 |
| 6,224,581 B1 * | 5/2001 | Withers | ........ | A61F 5/445 604/332 |
| 6,726,667 B2 * | 4/2004 | Leise, Jr. | ........ | A61F 5/445 604/335 |
| 7,008,407 B1 * | 3/2006 | Kamp | ........ | A61F 5/4405 604/327 |
| 7,476,220 B2 * | 1/2009 | Lillegaard | ........ | A61F 5/4404 604/338 |
| D649,241 S * | 11/2011 | Kunishige | ........ | D24/129 |
| 8,292,858 B2 * | 10/2012 | Burgess | ........ | A61F 5/4405 604/326 |
| 8,882,732 B2 * | 11/2014 | March | ........ | A61F 5/445 604/332 |
| 9,333,110 B2 * | 5/2016 | March | ........ | A61F 5/445 |
| 10,251,770 B2 * | 4/2019 | Chang | ........ | A61F 5/445 |
| 11,065,144 B2 * | 7/2021 | Nielsen | ........ | A61F 5/4407 |
| D978,345 S * | 2/2023 | Green | ........ | D24/129 |
| 11,957,615 B2 * | 4/2024 | Scalise | ........ | A61F 5/4407 |
| 2005/0273065 A1 * | 12/2005 | Lillegaard | ........ | A61F 5/4405 604/332 |
| 2009/0163883 A1 * | 6/2009 | Christensen | ........ | A61F 5/441 604/328 |
| 2012/0130329 A1 * | 5/2012 | March | ........ | F16K 3/24 604/332 |
| 2013/0338616 A1 * | 12/2013 | Galindo | ........ | A61F 5/4405 604/335 |
| 2015/0025483 A1 * | 1/2015 | March | ........ | A61F 5/4405 604/318 |
| 2015/0190272 A1 * | 7/2015 | Chang | ........ | A61F 5/445 604/335 |
| 2020/0046543 A1 * | 2/2020 | Scalise | ........ | A61F 5/445 |
| 2021/0022911 A1 * | 1/2021 | Scalise | ........ | A61F 5/445 |
| 2021/0251795 A1 * | 8/2021 | Holroyd | ........ | A61F 5/4405 |
| 2021/0251796 A1 * | 8/2021 | Holroyd | ........ | A61F 5/445 |
| 2021/0251797 A1 * | 8/2021 | Holroyd | ........ | A61F 5/4405 |
| 2021/0259874 A1 * | 8/2021 | Oellgaard | ........ | A61F 5/44 |
| 2024/0207083 A1 * | 6/2024 | Scalise | ........ | A61F 5/4407 |

OTHER PUBLICATIONS

Written Opinion issued by ISA/EPO in connection with PCT/US2019/025147 dated Sep. 24, 2019.

International Preliminary Report on Patentability and Written Opinion issued by ISA/EPO in connection with PCT/US2019/025147 dated Nov. 17, 2020.

* cited by examiner

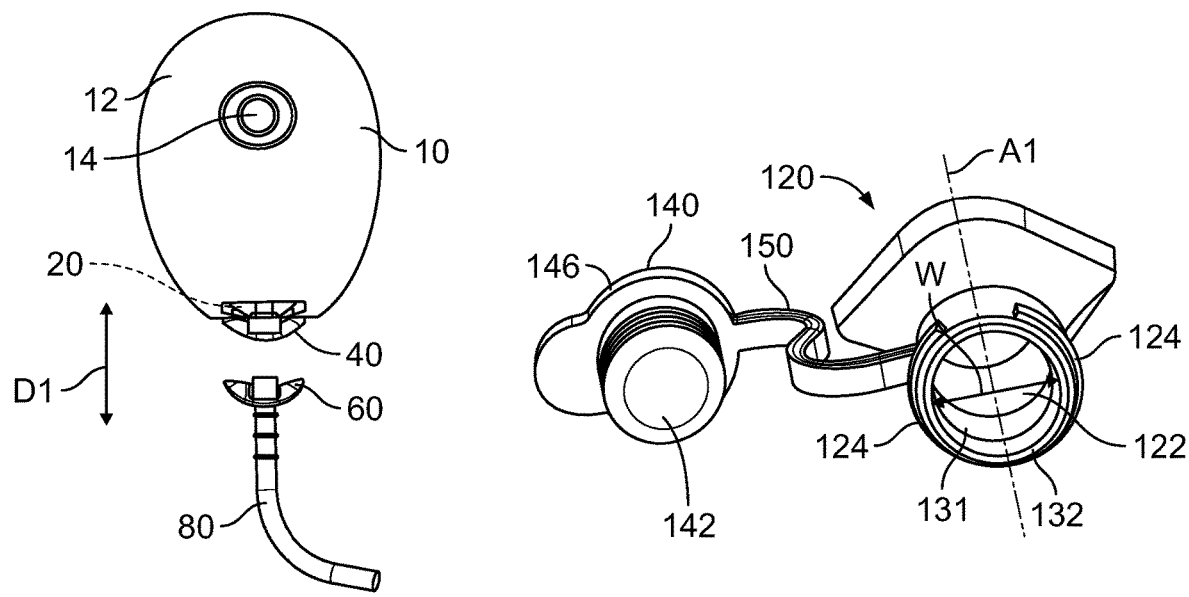
FIG. 1
FIG. 2
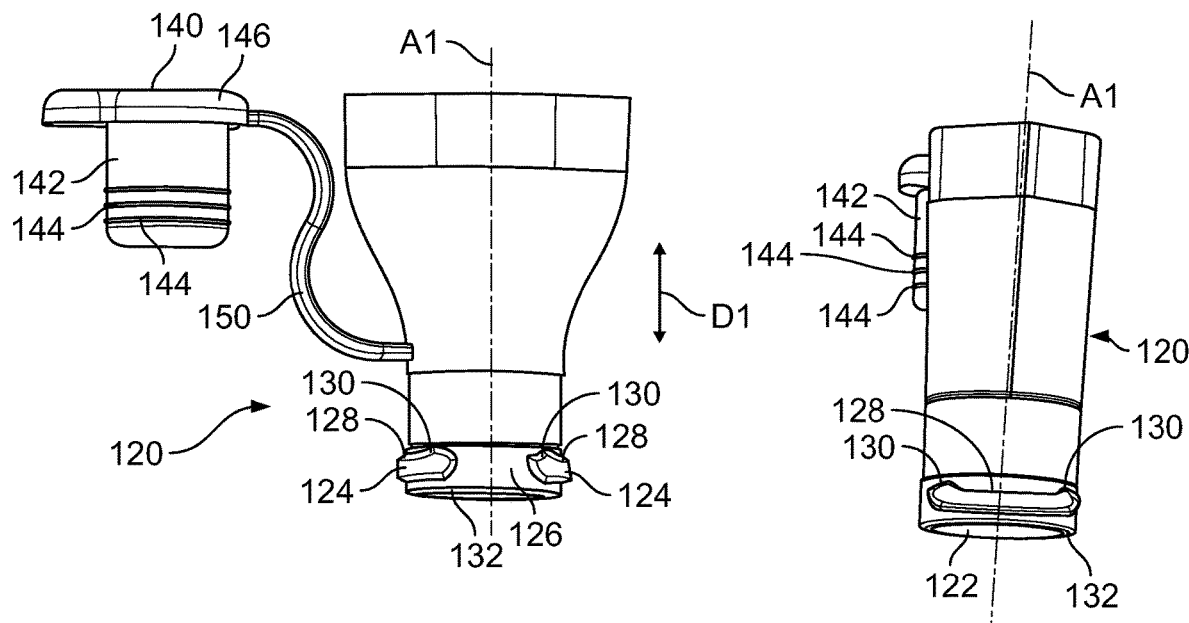
FIG. 3
FIG. 4

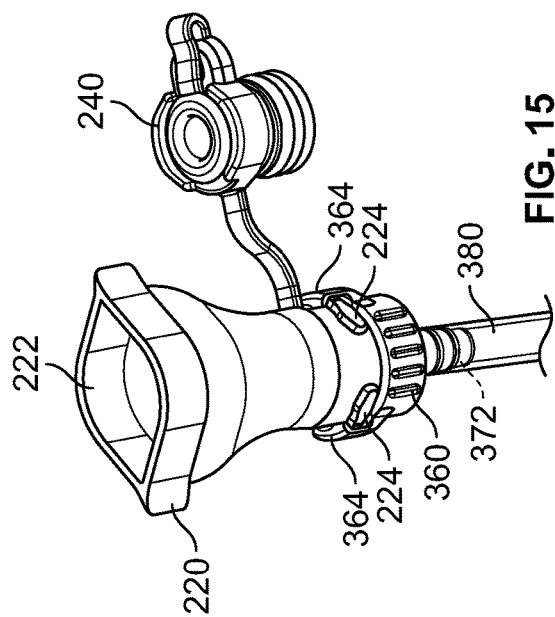
FIG. 15
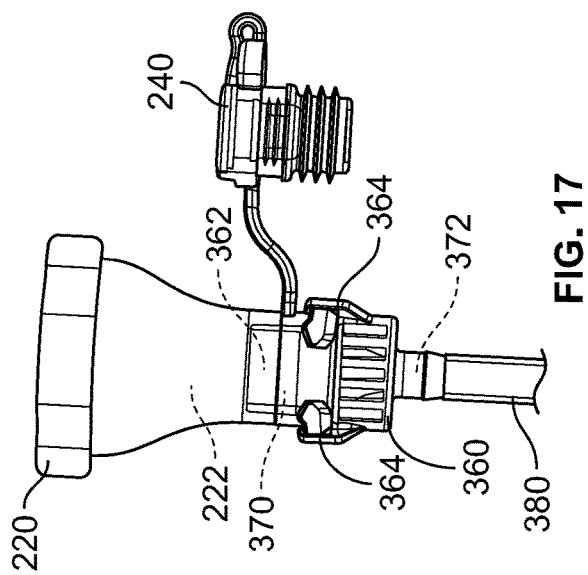
FIG. 17
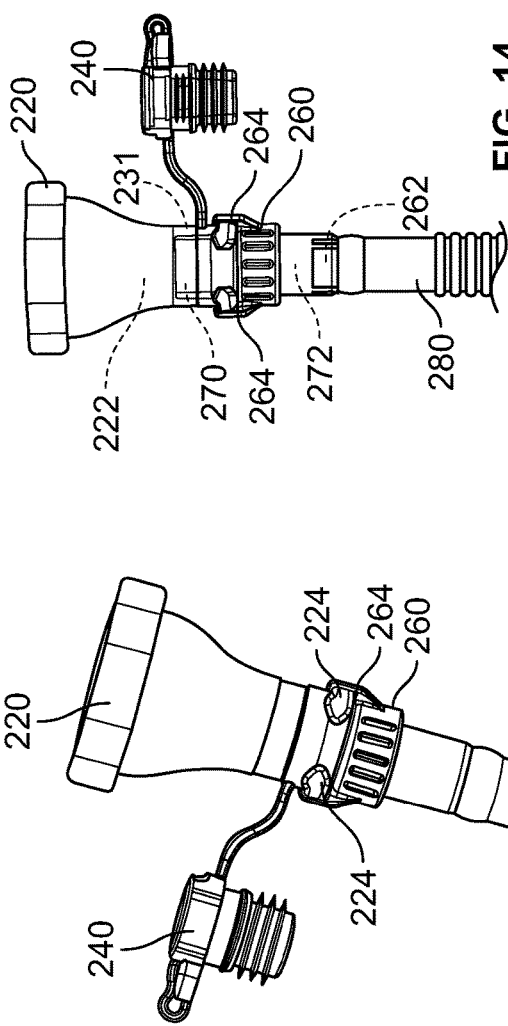
FIG. 14
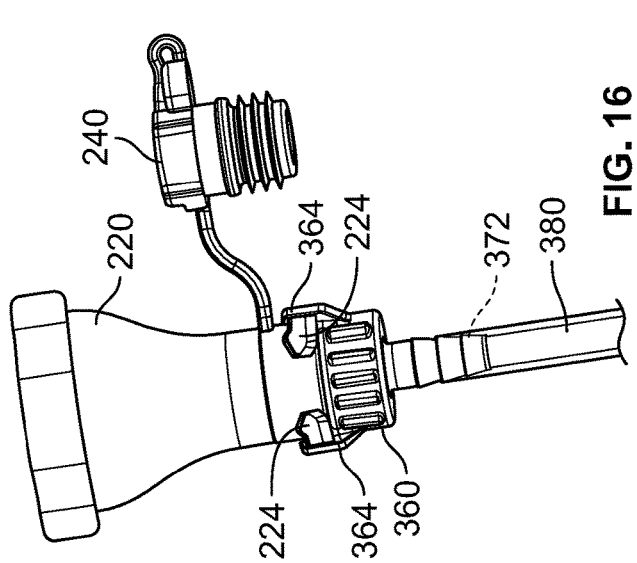
FIG. 16
FIG. 13

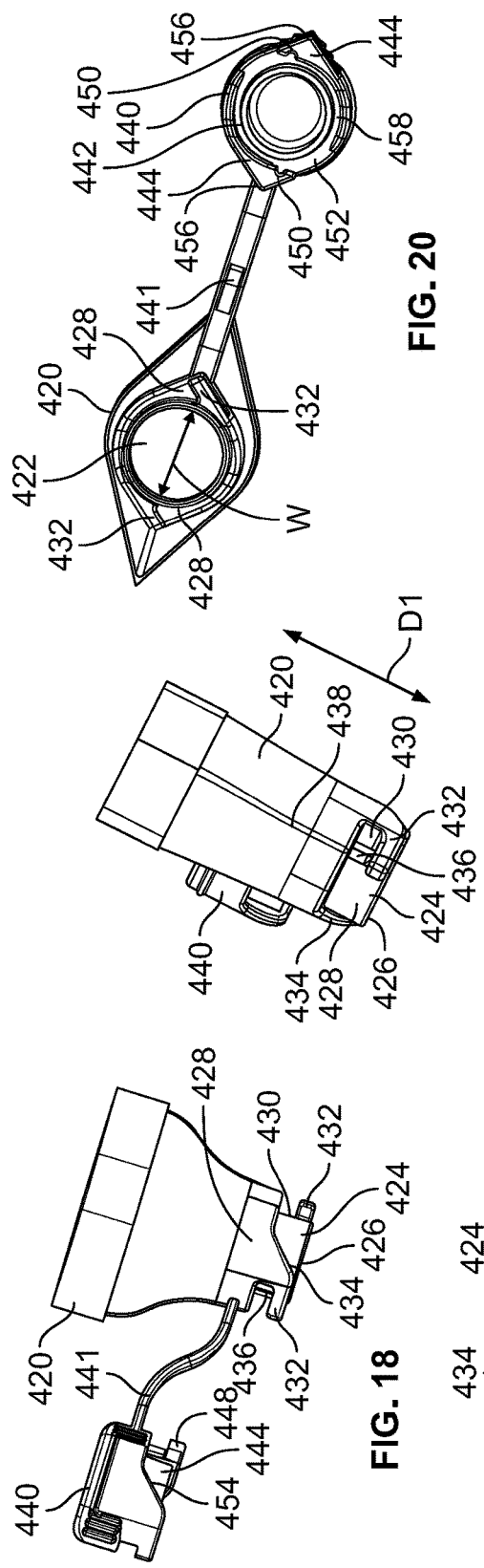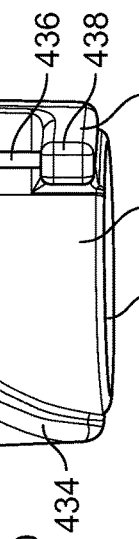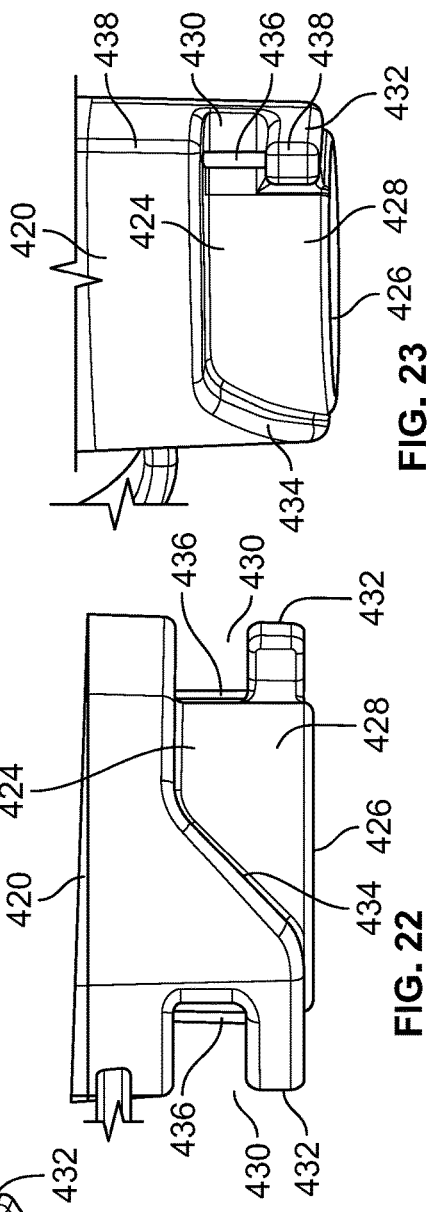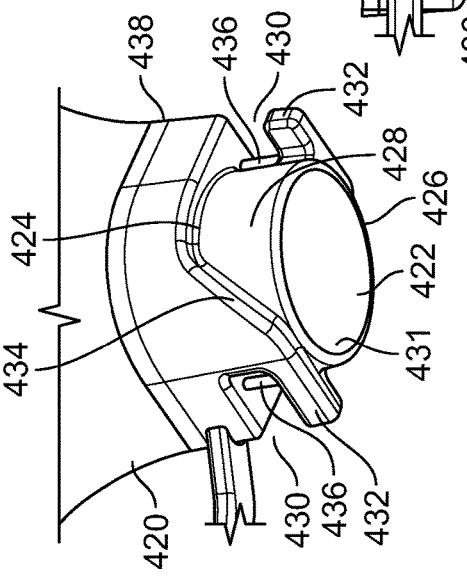

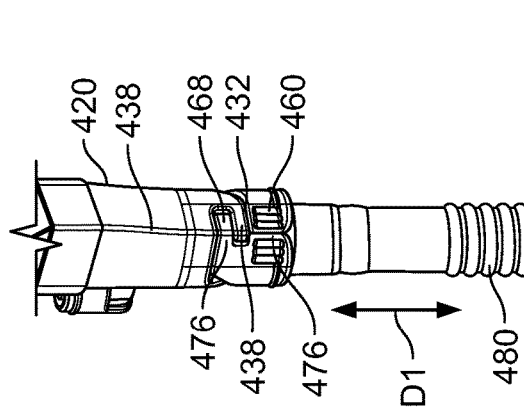
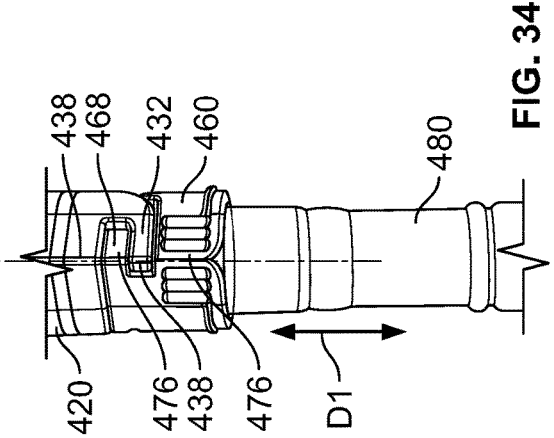
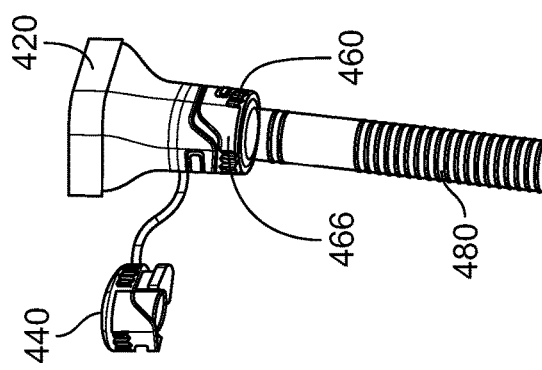
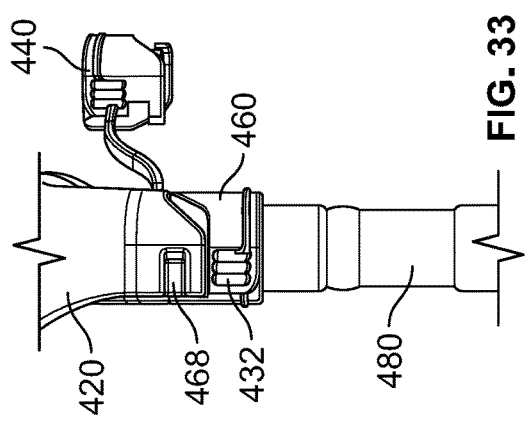
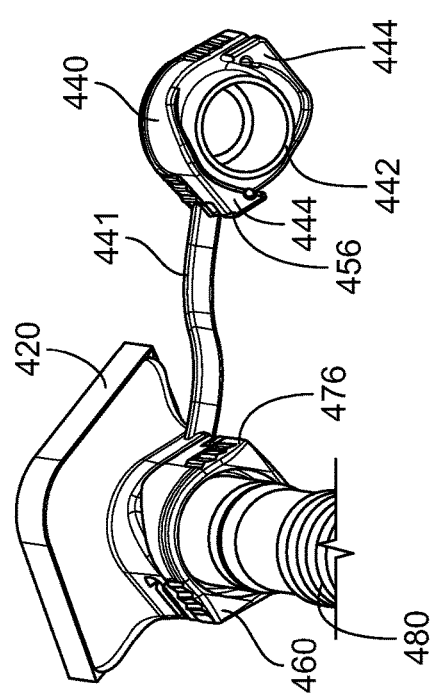
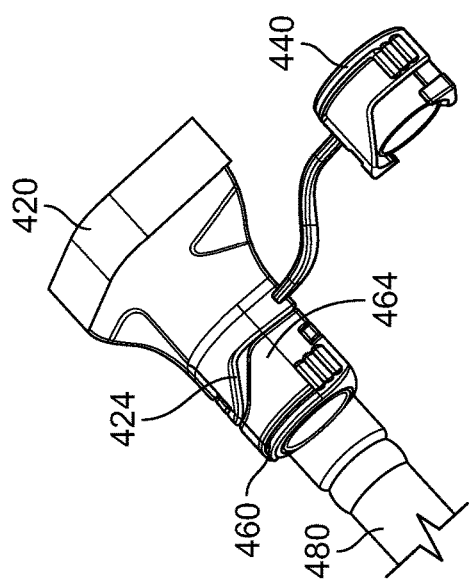
FIG. 29
FIG. 30
FIG. 31
FIG. 32
FIG. 33
FIG. 34

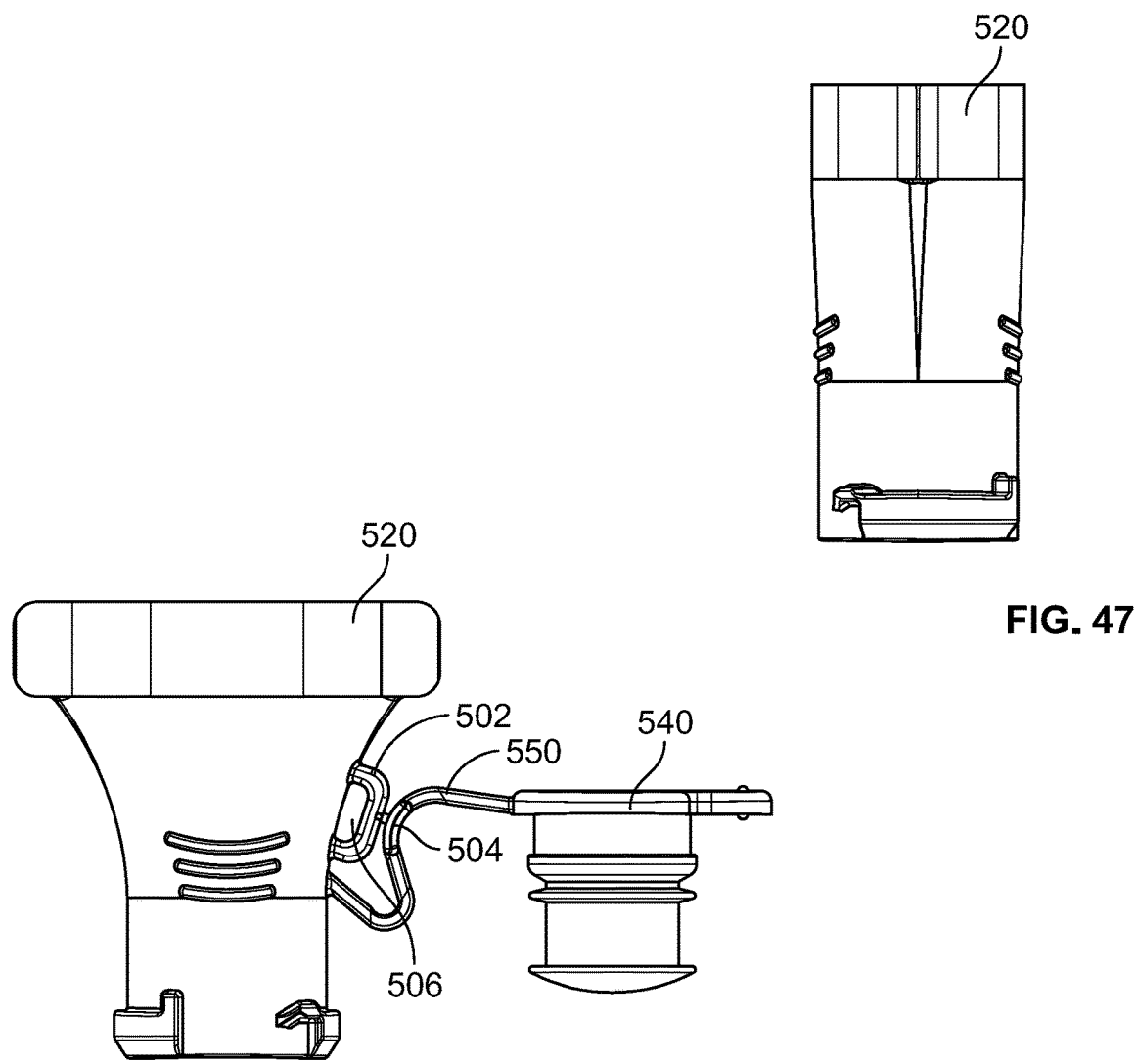
FIG. 47
FIG. 48
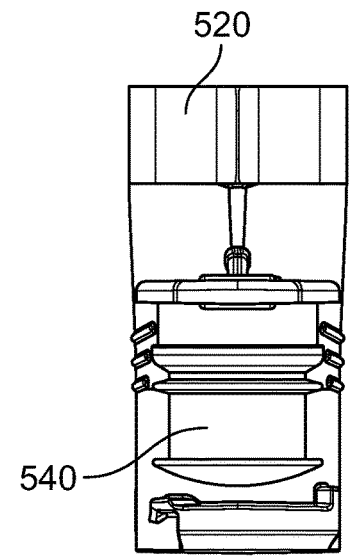
FIG. 49

OSTOMY COLLECTION AND DRAINAGE SYSTEM

CROSS-REFERENCE TO RELATED APPLICATIONS

This application is a Continuation of U.S. application Ser. No. 16/980,264, filed Sep. 11, 2020, which claims the benefit of and priority to International Patent Application No. PCT/US2019/025147, filed Apr. 1, 2019, which claims the benefit of and priority to U.S. Provisional Application No. 62/673,108, filed May 17, 2018, the contents of which are incorporated fully herein by reference.

BACKGROUND

The following description relates generally to an ostomy appliance, and in particular, an ostomy system having a pouch, outlet body, and a closure and an adapter configured to be interchangeably coupled to the outlet body.

An ostomy pouch typically includes opposing side walls defining an internal collection area. One of the side walls is provided with an opening to receive a stoma, and means to secure the pouch to the user, such as an adhesive barrier, so that bodily waste discharged through the stoma is received within the collection area without leakage from the stoma/barrier/pouch environment.

A drainable ostomy pouch may further include a drainage port at a lower end of the pouch. In a known drainable ostomy pouch, the drainage port is formed as a narrowed neck portion having an opening extending therethrough. The drainage port is operable between a closed condition and an open condition. In the closed condition, the drainage port is configured to substantially seal the lower end of the drainable ostomy pouch so that bodily waste may be securely collected and stored in the collection area. In the open condition, the bodily waste may flow from the collection area through the opening to be drained from the ostomy pouch.

Alternatively, the drainable ostomy pouch may be part of an ostomy drainage system, such as a night drainage system or other high volume drainage system. In an ostomy drainage system, the discharge port is coupled to a hose, and the hose is connected to a relatively larger volume drainage bag. Thus, the contents may flow from the ostomy pouch, through the opening of the discharge port and the hose, to be received in the drainage bag. Accordingly, the ostomy drainage system has increased storage capacity relative to the ostomy pouch alone and may require less frequent emptying.

In a known drainable ostomy pouch, the drainage port may be formed continuously with the side walls. To close the drainage port, the neck portion may be folded or rolled and held in place with a fastener. In the closed condition, the opening in the discharge port is substantially closed to seal against egress of the pouch contents (i.e., the bodily waste) through the discharge port. The discharge port may be moved to the open condition by releasing the fastener and unrolling or unfolding the neck portion. However, an ostomy pouch with this type of discharge port is difficult to connect to a hose in a drainage system because the discharge port lacks rigidity. In addition, folding or rolling the discharge port, and subsequent fastening, as described above, may be time consuming and difficult for some users with limited dexterity. Further, it may be difficult to determine when the discharge port is adequately closed to seal against unwanted egress of pouch contents.

In another drainable ostomy pouch, the discharge port may include an outlet body. The outlet body is formed of a thicker, more rigid material than the side walls of the ostomy pouch and is connected to the side walls, for example, by heat sealing. The opening in the discharge port extends into the outlet body. The opening may extend through an end of the outlet body to allow for egress of the pouch contents through the outlet body in the open condition. In a closed condition, a cap or plug may be friction fit over or fitted into the opening in the outlet body. When the drainable ostomy pouch is used in an ostomy drainage system, an adapter may be friction fit to the outlet body and a hose may be connected to the adapter. Accordingly, the pouch contents may drain through the adapter and hose.

Alternatively, the opening may terminate at a normally closed slit at the end of the outlet body. The slit may form a squeeze valve, whereby in response to application of opposing, inwardly directed forces, the slit opens to allow for egress of the pouch contents. In the closed condition, a cap may be friction fit over the end of the outlet body to further seal against unwanted egress. When the drainable ostomy pouch having the outlet body described above is used in an ostomy drainage system, the discharge port may be moved to the open condition by squeezing the outlet body, and an adapter connected to a hose inserted into the opening, through the open slit, to be friction fit to the outlet body.

However, in the discharge ports above, it may be difficult for a user to confirm an adequate coupling between the outlet body and the cap, plug or adapter. In addition, the friction fit coupling between the outlet body and the cap, plug or adapter described above may be overcome by application of a force in a direction which moves the cap, plug or adapter away from the outlet body, or vice versa. It has been found that in some instances, inadvertent or accidental contact with a component of the ostomy drainage system may be sufficient to overcome the friction fit coupling, thereby causing the outlet body and the cap, plug or adapter to inadvertently separate from one another, leading to unintended drainage or emptying of the ostomy pouch.

Further, a wearer may find the outlet body to be uncomfortable. For example, because of the relatively more rigid construction of the outlet body, a corner or edge of the outlet pressed against the wearer's skin may cause discomfort. Further still, a relatively soft or flexible discharge port of the type that may be rolled or folded, or a discharge port including a valve structure, such as a squeeze valve, may be susceptible to clogging.

Accordingly, it is desirable to provide an ostomy collection and drainage system in which feedback may be provided to the user to confirm coupling between an outlet body and a closure or adapter. It is also desirable to provide an ostomy collection and drainage system that is comfortable to the wearer, is unlikely to clog, and is resistant to inadvertent separation between the outlet body and the closure or adapter.

SUMMARY

According to one aspect, an ostomy collection and drainage system may include an ostomy pouch having an outer wall defining an internal collection area, an inlet opening formed in the outer wall in fluid communication with the internal collection area, an outlet body connected to the outer wall and having an outlet opening extending therethrough in fluid communication with the internal collection area, the outlet body having one of a latch and a catch, a closure configured for removable coupling to the outlet body and an adapter configured for removable coupling to the outlet body, the adapter having an adapter opening extending therethrough and the other of the latch and the catch. The adapter and the closure may be interchangeably coupled to the outlet body such that in a first condition the adapter is coupled to the outlet body by way of engagement of the catch and the latch, and in a second condition the closure is coupled to the outlet body.

In an embodiment, the ostomy collection and drainage system may comprise a flexible member extending between the closure and the outlet body to connect the closure to the outlet body.

The closure may comprise a first plug, wherein the closure may be coupled to the outlet body by way of frictional engagement of the first plug with the outlet body in the outlet opening in the second condition. In an embodiment, the first plug may include a first plug opening extending therethrough, and the closure may also comprise a second plug removably coupled to the first plug by way of friction engagement with the first plug in the first plug opening. The ostomy collection and drainage system may further comprise a first flexible member extending between the first plug and the outlet body to connect the first plug to the outlet body, and a second flexible member extending between the second plug and the first plug to connect the second plug to the first plug.

In an embodiment, the closure may include a second of the catch or latch that is formed on the adapter. In any of the foregoing embodiments, the catch and the latch may be engaged in a rotational direction in an interference fit and form a mechanical interlock to restrict movement in an axial direction of the adapter relative to the outlet body.

In an embodiment, the outlet body may comprise the catch and the adapter may comprise the latch. The catch may project radially outward, extending in a peripheral direction along a periphery of the outlet body, and include a first surface. The latch may extend in an axial direction and include an inwardly extending projection at a free end that is configured to engage the first surface to form a mechanical interlock and restrict movement in an axial direction of the adapter relative to the outlet body. The first surface may comprise two peaks spaced from one another in the peripheral direction. The inwardly extending projection may be configured for interfering movement over the peaks for positioning between the two peaks in the first condition.

In another embodiment, the catch may be a recess comprising a first portion extending from an axial end of the outlet body, and a second portion, connected to the first portion, extending in a peripheral direction along a periphery of the outlet body and spaced from the axial end of the outlet body. The latch may comprise a base and a lug connected to the base, wherein in the first condition, the base is received in the first portion of the catch and the lug is received in the second portion of the catch. The catch may also comprise a protrusion formed in the first portion or the second portion and the latch may comprise a notch, wherein the notch and the protrusion may be engaged in an interference fit with one another in the first condition.

The second portion may be spaced from the axial end of the outlet body by an arm, and the adapter may include a groove formed between the lug and an axial face, wherein the groove receives the arm in the first condition to form a mechanical interlock and restrict movement in an axial direction of the adapter relative to the outlet body. The closure may also comprise a second latch. The second latch may include a second base and a second lug connected to the second base, a second notch, and a second groove formed between the second lug and a second axial face. In the second condition, the second base may be received in the first portion of the catch and the second lug may be received in the second portion of the catch. The second notch and the protrusion may be engaged in an interference fit with one another in the second condition. The second groove may receive the arm in the second condition to form a second mechanical interlock and restrict movement in the axial direction of the closure relative to the outlet body. The closure may further comprise an inner collar disposed radially inward of the second tab. The inner collar may be configured to engage the outlet body within the outlet opening.

In an embodiment, the catch may include a foot formed at a free end, and the latch may include a recess having a shoulder formed therein. The foot may be disposed in the recess and engage the shoulder in an interference fit in the first condition to form a mechanical interlock and restrict movement in an axial direction of the adapter relative to the outlet body. The closure may further include a second latch having a second recess including a second shoulder formed therein, wherein the foot is disposed in the second recess and engages the second shoulder in an interference fit in the second condition to form a second mechanical interlock and restrict movement in the axial direction of the closure relative to the outlet body.

In any of the foregoing embodiments, engagement of the catch and the latch with one another may provide one or more of an audible and a tactile feedback to a user.

In an embodiment, the outlet body may comprise an alignment edge, the adapter may comprise an adapter alignment edge, and the closure may comprise a closure alignment edge. In such an embodiment, the alignment edge and the adapter alignment edge may be aligned to provide a visual feedback in the first condition. In the second condition, the alignment edge and the closure alignment edge may be aligned to provide a visual feedback.

In some embodiments, the ostomy collection and drainage system may include a closure docking system configured to hold the closure at a location proximate the outlet body away from the outlet opening. The closure docking system may comprise a first docking part and a second docking part, wherein the first and second docking parts are configured to engage with each other to fixedly hold the closure at the location.

In an embodiment, the first docking part may be formed as a handle like projection extending from the outlet body and defining an opening configured to receive the second docking part. The second docking part may be formed as a tab like projection extending from a side surface of the flexible member, wherein the closure docking system is configured to dock the closure by inserting the second docking part into the opening of the first docking part.

In another aspect, an outlet device for an ostomy pouch comprising an outlet body, a closure, and a closure docking system is provided. The outlet body may include an outlet opening extending therethrough, and the closure may be configured for removable coupling to the outlet body. The closure docking system may comprise a first docking part and a second docking part, wherein the first and second docking parts are configured to engage with each other to fixedly hold the closure at a location proximate the outlet body away from the outlet opening. In an embodiment, the closure may be tethered to the outlet body by a flexible member. In such an embodiment, the first docking part may be formed as a handle like projection extending from the outlet body and defining an opening configured to receive the second docking part, and the second docking part may be formed as a tab like projection extending from a side surface of the flexible member. The closure docking system may be configured to dock the closure by inserting the second docking part into the opening of the first docking part.

In another aspect, an ostomy pouch comprising an outer wall defining a cavity for collecting body waste, an inlet opening formed in the outer wall configured to receive a stoma, an outlet body, a closure and a closure docking system is provided. The outlet body may be connected to the outer wall and have an outlet opening extending therethrough in fluid communication with the cavity. The closure may be configured for removable coupling to the outlet body. The closure docking system may comprise a first docking part and a second docking part, wherein the first and second docking parts are configured to engage with each other to fixedly hold the closure at a location proximate the outlet body away from the outlet opening.

In an embodiment, the closure may be tethered to the outlet body by a flexible member. The first docking part may be formed as a handle like projection extending from the outlet body and defining an opening configured to receive the second docking part. The second docking part may be formed as a tab like projection extending from a side surface of the flexible member. The closure docking system may be configured to dock the closure by inserting the second docking part into the opening of the first docking part.

Other objects, features, and advantages of the disclosure will be apparent from the following description, taken in conjunction with the accompanying sheets of drawings, wherein like numerals refer to like parts, elements, components, steps, and processes.

BRIEF DESCRIPTION OF THE DRAWINGS

FIG. 1 is a diagram showing an ostomy collection and drainage system according to an embodiment described in herein;

FIG. 2 is a bottom perspective view of an outlet body configured for use in an ostomy collection and drainage system according to an embodiment;

FIG. 3 is a front perspective view of the outlet body of FIG. 2;

FIG. 4 is a side perspective view of the outlet body of FIG. 2;

FIG. 13 is a front view of the assembly of FIG. 12;

FIG. 14 is a transparent view of the assembly of FIG. 12;

FIG. 15 is a perspective view showing another assembly of the outlet body and closure of FIG. 9, coupled to an adapter and drainage tube, according another embodiment;

FIG. 16 is a front view of the assembly of FIG. 15;

FIG. 17 is a transparent view of the assembly of FIG. 16;

FIG. 18 is a front perspective view of an outlet body and closure configured for use in an ostomy collection and drainage system, according to another embodiment;

FIG. 19 is a side view of the outlet body of FIG. 18;

FIG. 20 is a bottom perspective view of the outlet body and closure of FIG. 18;

FIG. 21 is an enlarged view of a portion of the outlet body of FIG. 18;

FIG. 22 is another enlarged view of a portion of the outlet body of FIG. 18;

FIG. 23 is another enlarged view of a portion of the outlet body of FIG. 18;

FIG. 29 is a bottom perspective view showing an assembly including the outlet body of FIG. 18 coupled to the adapter and drainage tube of FIG. 26, according to an embodiment;

FIG. 30 is a front view of the assembly of FIG. 29;

FIG. 31 is a side view of the assembly of FIG. 29;

FIG. 32 is another perspective view of the assembly of FIG. 29;

FIG. 33 is an enlarged side perspective view of a portion of the assembly of FIG. 29;

FIG. 34 is an enlarged perspective side view of a portion of the assembly of FIG. 29;

FIG. 47 is a side view of the outlet body of FIG. 46;

FIG. 48 is a front view of the outlet body of FIG. 46; and

FIG. 49 is another side view of the outlet body of FIG. 46.

DETAILED DESCRIPTION

Figure 5:
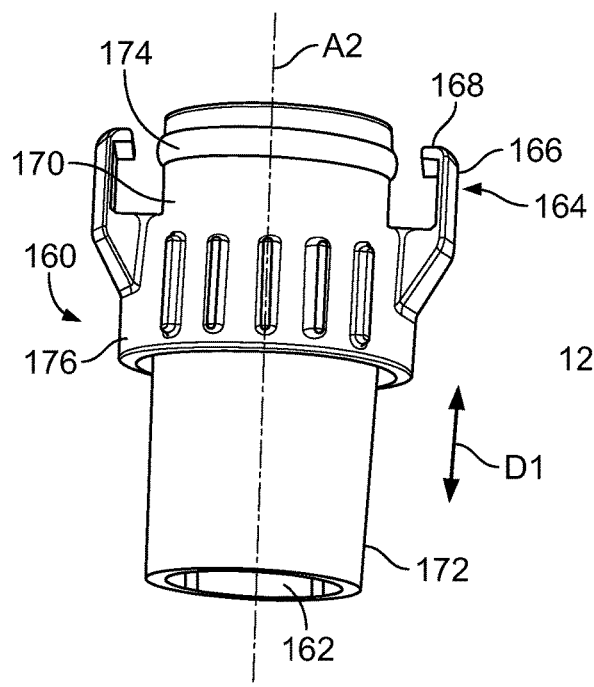
FIG. 5 is a front perspective view of an adapter configured for use in an ostomy collection and drainage system, according to an embodiment.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

Referring to FIG. 1, an ostomy collection and drainage system 5 includes an ostomy pouch 10 having an outer wall 12 defining an internal volume to form an internal collection area (not shown). The outer wall 12 may have an inlet opening 14 formed therein. The inlet opening 14 is disposed in fluid communication with the internal collection area and is configured to receive a stoma so that a discharge from the stoma may be received in the internal collection area and stored in the internal collection area as contents of the ostomy pouch 10. The inlet opening 14 may be positioned at an upper portion of the ostomy pouch 10.

An outlet body 20 is secured to the outer wall 12. In one embodiment, the outlet body 20 is positioned at a lower portion of the ostomy pouch 10 and is configured to selectively allow drainage of the contents from the internal collection area, to seal against drainage of the contents from the internal collection area, and to connect to a high volume drainage system, such as a night drainage system, described further below. In one embodiment, the outlet body 20 may be secured to the outer wall 12 for example, by heat sealing, with an adhesive, or by being formed together with the outer wall 12, for example in a molding process, such as a two-shot molding process. Preferably, the outlet body 20 is secured to the outer wall 12 in such a way that a seal is formed between the outlet body 20 and the outer wall 12, to prevent or limit undesired leakage of the contents between the outer wall 12 and the outlet body 20.

The ostomy collection and drainage system 5 further includes a closure 40 and an adapter 60, each configured for removable and interchangeable coupling to the outlet body 20. In one embodiment, the closure 40 and the adapter 60 are interchangeably coupled to the outlet body 20 such that in a first condition the adapter 60 is coupled to the outlet body 20 and in a second condition the closure 40 is coupled to the outlet body 20. In one embodiment, the closure 40 and the adapter 60 may be interchangeably coupled to the outlet body 20 by way of a latch engaging a catch in friction or interference fit, including a snap fit, and optionally, a mechanical interlock to restrict movement of the closure 40 or adapter 60 relative to the outlet body 20, for example, in an axial or substantially axial direction D1. A tube 80 may be connected to the adapter 60 to fluidically connect the ostomy pouch 10 to, for example, a night drainage bag (not shown).

FIG. 2 is a bottom perspective view of an outlet body 120 configured for connection to an ostomy pouch 10 in an ostomy collection and drainage system, according to an embodiment described herein. FIG. 3 is a front view of the outlet body 120 of FIG. 2. Referring to FIGS. 2 and 3, the outlet body 120 generally includes an outlet opening 122 through which contents of the ostomy pouch 10 may be drained. The outlet opening 122, in one embodiment, extends along a first axis A1. In one embodiment, the outlet opening 122 may have a width or diameter W of about 15 mm to about 25 mm. For example, in one embodiment, the outlet opening 122 may have a width or diameter W of about 16 mm to about 19 mm.

FIG. 4 is another side view of the outlet body 120 of FIG. 2. With reference to FIGS. 2-4, the outlet body 120 includes one of a latch and a catch, which are configured for releasable engagement with one another as described further below. In one embodiment, the catch 124 is formed on the outlet body 120. The catch 124 may be formed as a projection which extends radially outward and in a peripheral direction along at least a portion of a periphery on the outlet body 120. In one embodiment, the outlet body 120 includes two catches 124 similarly formed and spaced apart from one another by a gap 126 in the peripheral direction.

In one embodiment, the catch 124 includes a first surface 128 which may be an upper surface of the catch 124. It is understood however, that the directional term "upper" does not limit the outlet body 120 and the catch 124 to a particular orientation, but rather, is used only as example consistent with the orientation of the outlet body 120 and catch 124 as shown in the drawings. In one embodiment, the catch 124 includes at least one peak 130 formed as a section of increased height extending upwardly on the first surface 128. In one embodiment, the catch 124 includes two peaks 130 spaced apart in the peripheral direction on the outlet body 120.

As more clearly shown in FIGS. 2 and 3, a closure 140 is configured for removable coupling to the outlet body 120. For example, the closure 140 may be removably coupled to the outlet body 120 by way of a frictional engagement with the outlet body 120 in the outlet opening 122. In one embodiment, the closure 140 includes a plug 142 having an outer surface configured to frictionally engage an inner surface 131 around the outlet opening 122. Preferably, the frictional engagement between the plug 140 and the inner surface 131 is a sealed engagement to substantially prevent or limit unintended egress of the contents through the outlet opening 122. In one embodiment, the plug 142 may include one or more ribs 144. The one or more ribs 144 may extend either partially or entirely about an outer periphery on the plug 140.

Referring still to FIGS. 2 and 3, the closure 140 may also include a cap 146 configured, in one embodiment, to engage an axial end 132 of the outlet body 120 when the plug 142 is engaged in the outlet opening 122, i.e., in the second condition. The cap 146 may be formed having a width greater than a width of the plug 142. In one embodiment, the cap 146 and the plug 142 are formed as a single, continuous unit. Further still, in one embodiment, the closure 140 may be connected to the outlet body 120 with a flexible member 150, such as a strap or living hinge.

Accordingly, in the embodiments shown in FIGS. 2-4, the closure 140 may be coupled to the outlet body 120 by positioning the plug 142 in the outlet opening 122 in frictional engagement with the inner surface 131. With the closure 140 so positioned, the ostomy pouch 10 is configured to collect and store discharge from a stoma. With the closure 140 removed from the outlet opening 142, the contents (i.e., the stoma discharge) may be drained from the ostomy pouch 10 through the outlet opening 122.

FIG. 5 is a front perspective view of an adapter 160 according to an embodiment described herein. The adapter 160 includes an adapter opening 162 extending therethrough. In one embodiment, the adapter opening 162 extends on a second axis A2.

The adapter 160 includes the other of the latch and the catch that is formed on the outlet body 120. For example, in one embodiment, the adapter 160 includes a latch 164 configured to releasably engage the catch 124. In one embodiment, the adapter 160 may include two or more latches 164. In one embodiment, the number of latches 164 is equal to the number of catches 124, but the present disclosure is not limited to such an embodiment. In addition, it is understood that in another embodiment the outlet body 120 may be formed with the latch 164 and the adapter 160 may be formed with the catch 124.

The latch 164 and the catch 124 are configured for releasable engagement with one another by way of a friction or interference fit, including a snap fit, to couple the adapter 60 and outlet body 120 together. In addition, the latch 164 and the catch 124 may form a mechanical interlock to resist movement in, or substantially in, the axial direction D1 of the adapter 160 relative to the outlet body 120. In one embodiment, the latch 164 and the catch 124 may be brought into engagement by way of rotational movement relative to one another. In one embodiment, the relative rotational movement brings the latch 164 and catch 124 into a position where the mechanical interlock is formed, and the adapter 160 is coupled to the outlet body 120.

In one embodiment, the latch 164 includes a first portion 166 extending generally in the axial direction D1. The latch 164 may also include a second portion 168, formed as an inward projection, such as a hook, at a free end of the first portion 166.

Referring still to FIG. 5, the adapter 160 includes a first collar 170 and a second collar 172. In one embodiment, the first collar 170 is configured to frictionally engage the outlet body 120, for example, within the outlet opening 122. Preferably, the frictional engagement of the first collar 170 within the outlet opening 122 is a sealed engagement. The first collar 170 may include a peripherally extending bead 174 configured for engagement with the inner surface 131 to form a localized section of increased pressure against the inner surface 131.

Figure 6:
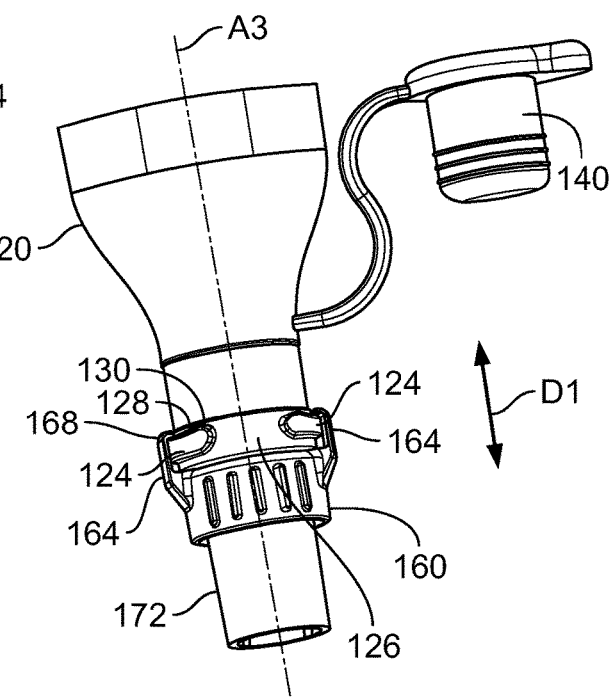
FIG. 6 is a perspective view showing an assembly in which the adapter of FIG. 5 is coupled to the outlet body of FIG. 2 according to an embodiment.

FIG. 6 is a perspective view of the adapter 160 coupled to the outlet body 120, according to an embodiment. Referring to FIG. 6, the adapter 160 may be coupled to the outlet body 120 by way of releasable engagement between the latch 164 and the catch 124, with the closure 140 removed from the outlet opening 122. In one embodiment, the adapter opening 162 and the outlet opening 122 may be axially aligned and extend on a common axis A3 through the coupled assembly adapter 160 and the outlet body 120.

The adapter 160 may be coupled to the outlet body 120 by moving the adapter 160 toward the outlet body 120, for example in the axial direction D1, to bring the first collar 170 into frictional engagement with the outlet body 120 within the outlet opening 122. The latch 164 may be moved, for example, in the axial direction D1 in the gap 126. The adapter 160 may be rotated to bring the latch 164 into interfering contact with one of the peaks 130 of the catch 124, thereby increasing resistance to the rotational movement. Continued rotational movement causes the latch 164 to deflect as it interferingly moves past the peak 130, and return to its relatively un-deflected condition upon clearing the peak 130. That is, rotation of the latch 164 past the peak 130 of the catch 124 brings the latch 164 and the catch 124 into an interference or snap fit engagement. The second portion 168 of the latch 164, formed as an inward projection, engages the first surface 128 of the catch 124 to form a mechanical interlock to resist movement in the axial direction D1 of the adapter 160 away from the outlet body 120.

In one embodiment, movement of the latch 164 into engagement with the catch 124, or vice versa, may provide an audible and/or tactile feedback to the user, in the form of a "click," "pop" or the like, which may be heard and/or felt by the user. Visual feedback may be provided to the user by way of visually inspecting the position of the latch 164 relative to the catch 124, for example, by determining that the latch 164 is positioned between the peaks 130. Accordingly, a user can confirm that the adapter 160 is coupled to the outlet body 120 by one or more of an audible, tactile, or visual confirmation.

To remove the adapter 160 from the outlet body 120, the adapter 160 may be rotated relative to the outlet body 120 to disengage the latch 164 from the catch 124. During disengagement, the latch 164 interfering moves past one of the peaks 130 in a manner similar to that described above. With the latch 164 positioned in the gap 126, the adapter 160 may be moved away from the outlet body 120, the first collar 170 may be removed from frictional engagement in the outlet opening 122, and the adapter 160 may be removed from the outlet body 120. Audible, tactile and or visual feedback may be provided to the user when removing the adapter in response to the interfering movement of the latch 164 out of the catch 124.

Figure 7:
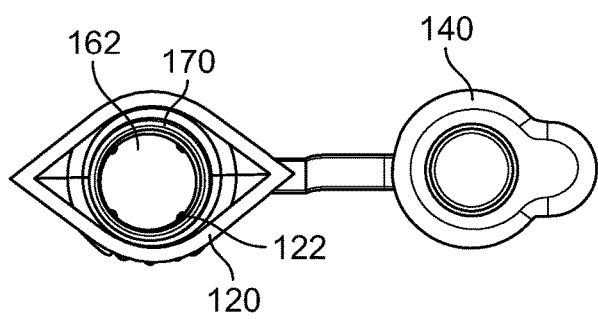
FIG. 7 is a top view of the assembly of FIG. 6.

FIG. 7 is a top view of the outlet body 120 coupled to the adapter 160, which corresponds to the first condition. Referring to FIG. 7, in one embodiment, the adapter opening 162 and the outlet opening 122 may co-extend on a common axis A3 (shown in FIG. 6).

Figure 8:
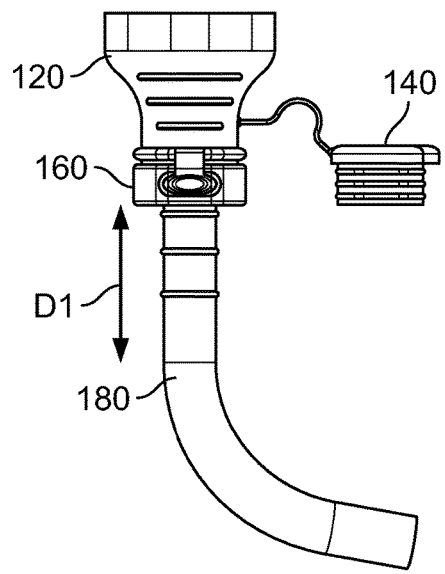
FIG. 8 is a front view showing an assembly of an outlet body, adapter and drainage tube coupled to one another, according to an embodiment.

FIG. 8 shows a drainage tube 180 connected to the adapter 160. In one embodiment, the second collar 172 (see FIGS. 5 and 6) may be positioned in the drainage tube 180 and frictionally engage the tube 180. Preferably, the frictional engagement is a sealed engagement. Alternatively, the adapter 160 and drainage tube 180 may be connected using other suitable techniques, such as heat sealing, adhesive fastening or mechanical fastening.

Referring to FIGS. 5, 6 and 8, for example, the adapter 160 may further include a gripping collar 176 positioned axially between the first collar 170 and the second collar 172. The gripping collar 176 is configured to be gripped by a user to manipulate the adapter 160 for example, for rotational and/or axial movement. In one embodiment, the latch 164 may extend from the gripping collar 176. The gripping collar 176 may have an outer width that is greater than an outer width of the first collar 170 and the second collar 172.

Figure 9:
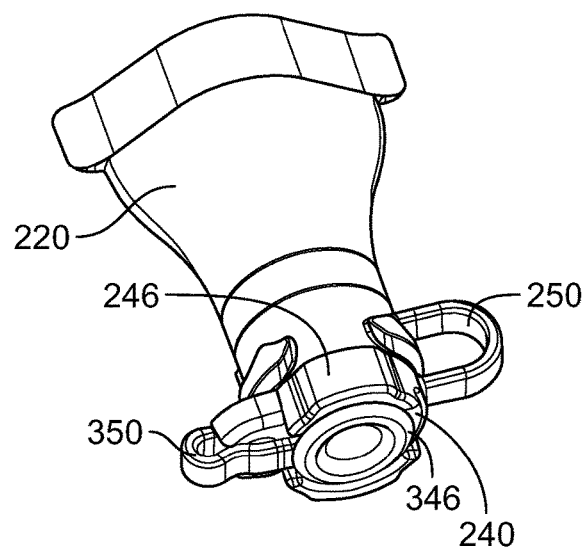
FIG. 9 is a perspective view of an outlet body having a closure according to another embodiment.
Figure 10:
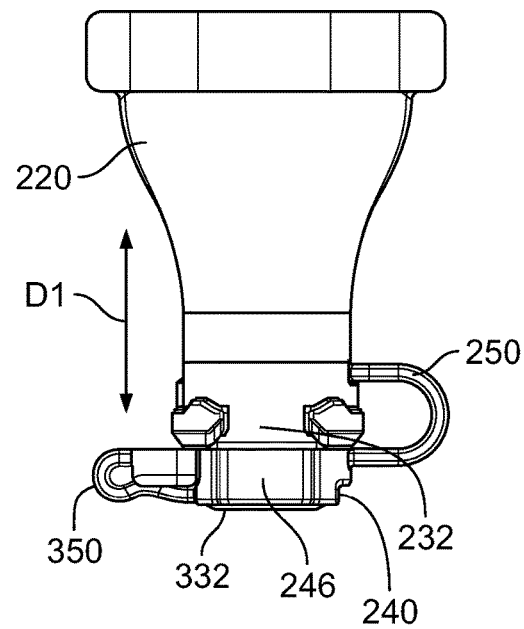
FIG. 10 is a front view of the outlet body and closure of FIG. 9.
Figure 11:
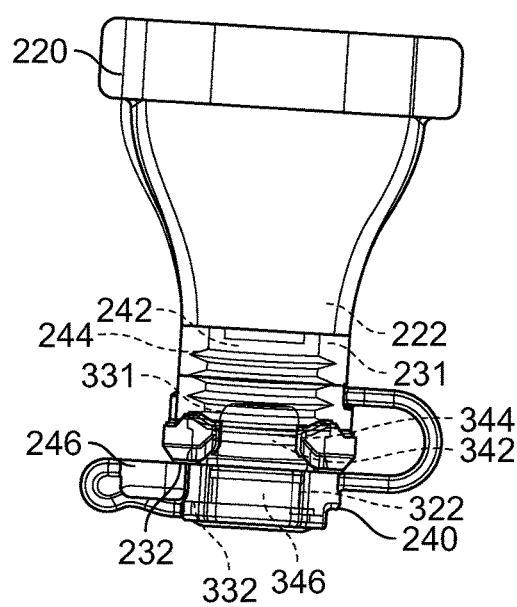
FIG. 11 is a transparent front view of the outlet body and closure of FIG. 9.

FIGS. 9-11 illustrate an outlet body 220 having a closure 240 according to another embodiment described herein. The outlet body 220 may be formed substantially the same as the outlet body 120 described above. Accordingly, further description of like parts of the outlet body 220 and the outlet body 120 may be omitted below.

FIG. 9 is a perspective view showing the closure 240 frictionally engaged in the outlet opening 222 of the outlet body 220, FIG. 10 is a front view showing the closure 240 frictionally engaged in the outlet opening 222 of the outlet body 220, and FIG. 11 is a front transparent view showing the closure 240 frictionally engaged in the outlet opening 222 of the outlet body 220, according to embodiments described herein.

Referring FIGS. 9-11, the closure 240 may be a two-part closure. For example, the closure 240 may include a first plug portion 242 (see FIG. 11) configured to be removably positioned and frictionally engaged in the outlet opening 222. In one embodiment, the first plug portion 242 may include one or more ribs 244 formed on an outer surface, configured to frictionally engage the inner surface 231 of the outlet body 220. The two-part closure 240 may also include a first cap 246 configured to engage an axial end 232 of the outlet body 220 when the first plug portion 242 is disposed in the outlet opening 222. The first cap 246 has a width that is greater than a width of the first plug portion 242. In one embodiment, the first plug portion 242 and the first cap 246 are formed as a single, continuous piece.

Still referring to the FIGS. 9-11, the two-part closure 240 may also include a second plug portion 342, optionally formed with one or more ribs 344 on an outer surface, and a second cap 346. The second cap 346 may have a width that is greater than a width of the second plug portion 342. As more clearly shown in FIG. 11, the first plug portion 242 and the first cap 246 include a closure opening 322 extending therethrough. With the first plug portion 242 positioned in the outlet opening 222, the closure opening 322 is disposed in communication with the outlet opening 222 and may receive the contents ostomy pouch 10 to drain the contents through the closure opening 322.

The second plug portion 342 is configured for removable positioning and frictional engagement in the closure opening 322. In addition, the second cap 346 is configured to engage an axial end 332 of the first cap 246. In one embodiment, the first cap 246 is formed with a recess or seat configured to receive at least a portion of the second cap 346. Preferably the frictional engagement between the first plug portion 242 and the inner surface 231 of the outlet body 220, and the frictional engagement between the second plug portion 342 and the inner surface 331 of the first plug portion 242 are sealed engagements.

In the embodiments shown in FIGS. 9-11, with the first and second plug portions 242, 342 positioned in the outlet opening 222 and the closure opening 322, respectively, the outlet body 220 may be substantially closed and sealed against egress of the contents from the ostomy pouch 10. Accordingly, the ostomy pouch 10 may collect and store the discharge from the stoma. One or both of the first and second plug portions 242, 342 may be removed from the outlet opening 222, or closure opening 322, respectively, to drain the contents from the ostomy pouch 10.

In one embodiment, the first plug portion 242 and the first cap 246 may be connected to the outlet body 220 by a first flexible member 250, such as a strap or a living hinge. The second plug portion 342 and the second cap 346 may be connected to the first plug portion 242 and the first cap 246 with a second flexible member 350, such as a second strap or second living hinge. In one embodiment, the closure member 240 may be formed as a single, continuous unit, for example, in a molding process.

Figure 12:
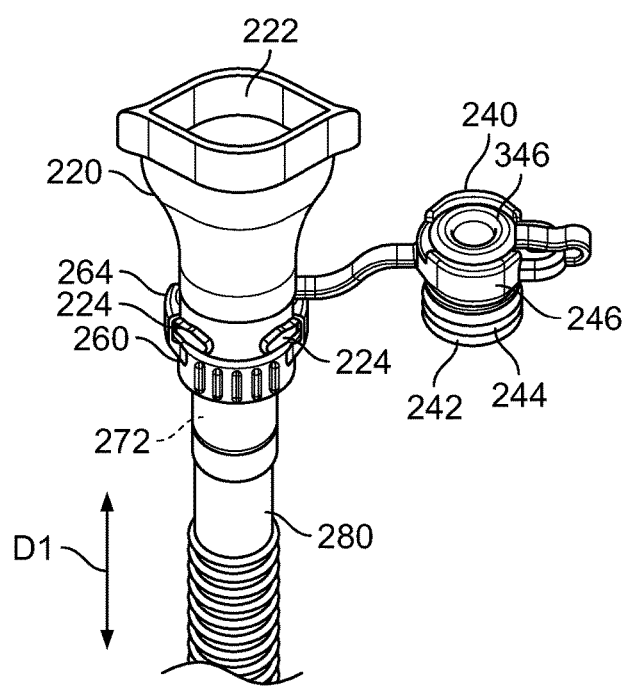
FIG. 12 is a perspective view showing an assembly of the outlet body and closure of FIG. 9, coupled to an adapter and drainage tube, according an embodiment.

FIGS. 12-14 show the outlet body 220 and closure 240 together with an adapter 260 and drainage tube 280, according to an embodiment described herein. In one embodiment, the adapter 260 is formed the same as the adapter 160 described above. Accordingly, further description of like parts in the adapter 260 and the adapter 160 may be omitted below.

FIG. 12 is a top perspective view of an assembly formed by the outlet body 220, closure 240, adapter 260 and drainage tube 280, according to an embodiment, and used in an ostomy collection and drainage system. FIG. 13 is a front view of the assembly shown in FIG. 12, and FIG. 14 is a transparent view of the assembly shown in FIG. 12, according to an embodiment. Referring to FIGS. 12-14, the closure 240 may be removed from frictional engagement with the outlet body 220 so that the contents of the ostomy pouch 10 may be drained through the outlet opening 222. The adapter 260 may be removably coupled to the outlet body 220 in the manner described above with respect to the adapter 160 and outlet body 120. That is, in one embodiment, the adapter 260 may be coupled to the outlet body 220 by way of engagement between the latch 264 and the catch 224. The resulting mechanical interlock between the latch 264 and the catch 224 resists relative axial movement. Frictional engagement of the first collar 270 in the outlet opening 222 also resists relative axial movement and preferably forms a sealed connection. Further, the second collar 272 may be frictionally engaged with the drainage tube 280.

Accordingly, in the embodiments shown in FIGS. 12-14, the contents of the ostomy pouch 10 may be drained through the outlet opening 222 of the outlet body 220, the adapter opening 262 of the adapter 260 and into the tube 280. The tube 280, at an end opposite to the adapter 260, may be coupled to a high volume bag, such as a night drainage bag (not shown).

FIGS. 15-17 show the outlet body 220 and closure 240 together with an adapter 360 and a tube 380, according to another embodiment described herein. FIG. 15 is a top perspective view of an assembly formed by the outlet body 220, closure 240, adapter 360 and tube 380, according to an embodiment. FIG. 16 is a front view of the assembly shown in FIG. 15, and FIG. 17 is a transparent view of the assembly shown in FIG. 15, according to an embodiment.

Referring to FIGS. 15-17, the closure 240 may be removed from frictional engagement with the outlet body 220 so that the contents of the ostomy pouch 10 may be drained through the outlet opening 222. The adapter 360 may be removably coupled to the outlet body 220 in the manner described above with respect to the adapter 160 and outlet body 120. That is, in one embodiment, the adapter 360 may be coupled to the outlet body 220 by way of engagement between the latch 364 and the catch 224, and frictional engagement of the first collar 370 in the outlet opening 222. Further, the second collar 372 may be connected with the tube 380 for example, in frictional engagement, by way of heat sealing, using an adhesive or mechanical fastener, or combinations thereof.

However, in the embodiments shown in FIGS. 15-17, the second collar 372 and tube 380 are sized and shaped for use in conjunction with a Foley catheter. For example, each of the second collar 372 and the tube 380 have a width, or diameter, that is less than a width, or diameter, of the second collar 272 and tube 280 in the embodiments above and shown in FIGS. 12-14. In addition, with reference to FIG. 16, for example, the second collar 372 may be formed having one or more sections of variable outer widths, or diameters. For example, each section may have a decreasing width from a first end to a second end.

FIGS. 18-20 show front, side and bottom perspective views, respectively, of an outlet body 420 and closure 440 according to another embodiment described herein. Referring to FIGS. 18-20, the outlet body 420 is configured for connection to the ostomy pouch 10 in the manner described above with respect to the outlet body 120. The outlet body 420 includes an outlet opening 422 configured to receive and allow draining of the contents from the ostomy pouch 10. The outlet opening 422 is defined at least in part by the inner surface 431 of the outlet body 420. In one embodiment, the outlet body 420 is formed with a catch 424 configured for removable engagement with a latch, as described further below. In one embodiment, the outlet body 420 includes two catches 424. In one embodiment, the outlet opening 422 may have a width or diameter W of 15 mm to 25 mm. For example, in one embodiment, the outlet opening 422 may have a width or diameter W of 16 mm to 19 mm.

FIGS. 21-23 are enlarged views showing different perspectives of the catch 424, according to an embodiment. Referring to FIGS. 18-23, the catch 424 is generally formed as a recess at or near an axial end 426 of the outlet body 420, and includes a first portion 428 open to the axial end 426 and a second portion 430 spaced from the axial end 426. In one embodiment, the second portion 430 may be spaced from the axial end 426 by an arm 432. A guide surface 434 may be formed along a portion of catch 424. The catch 424 may also include a protrusion 436. In one embodiment, the protrusion 436 is disposed in the second portion 430.

In one embodiment, the outlet body 420 may include an alignment edge 438 on an outer surface. The alignment edge 438 may define, for example, a line or curve, and may be formed as an angled or rounded corner, a channel or other external structural feature and/or visible marking. In one embodiment, the alignment edge 438 may extend substantially in the axial direction D1. The alignment edge 438 may include a first section extending on the outlet body, and a second section extending on the arm 432, aligned with the first section. In one embodiment, the protrusion 436 may be aligned with the alignment edge 438 as well.

Figure 26:
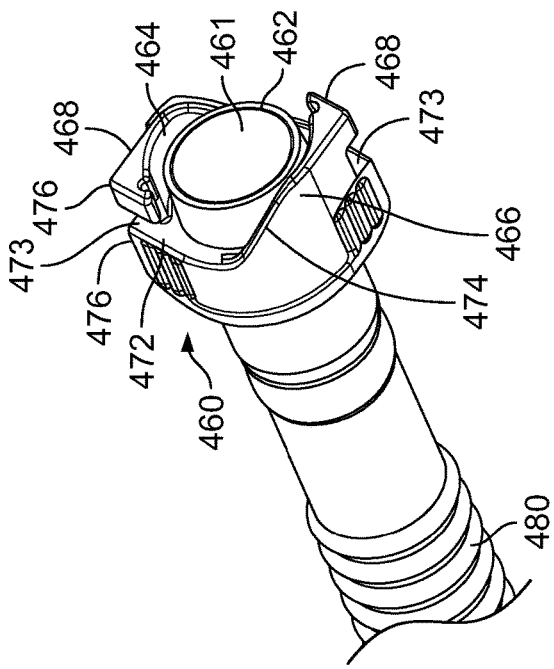
FIG. 26 is another perspective view of the assembly of FIG. 24.
Figure 25:
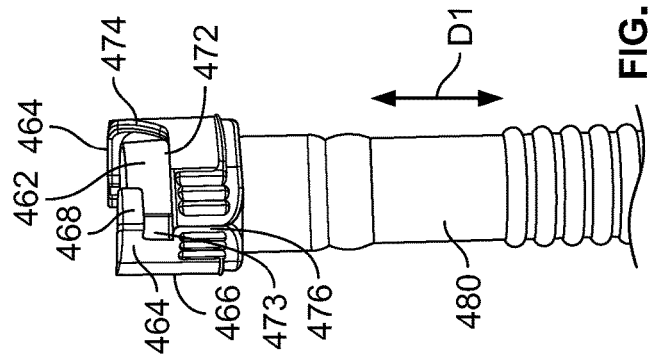
FIG. 25 is another perspective view of the assembly of FIG. 24.
Figure 24:
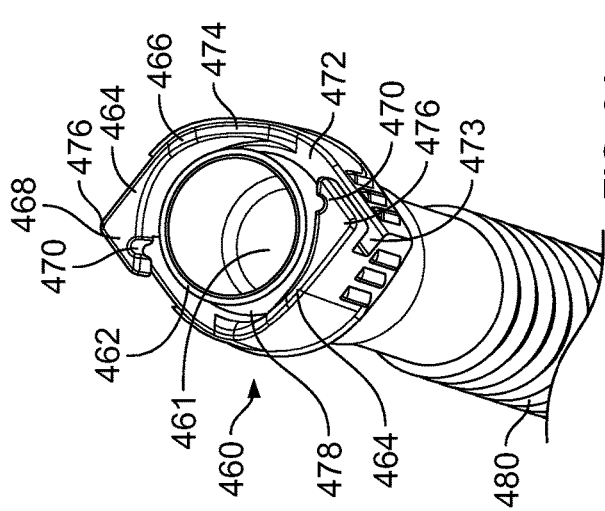
FIG. 24 is a perspective view showing an assembly of an adapter and a drainage tube configured for removable coupling with the outlet body of FIG. 18, according to an embodiment.

FIGS. 24-26 are perspective views of an adapter 460 configured for removable coupling with the outlet body 420 and connection to a drainage tube 480, according to an embodiment. Referring to FIGS. 24-26, the adapter 460 includes an adapter opening 461 extending therethrough, a first inner collar 462 around a portion of the adapter opening 461, and a first latch 464 having a first base 466 and a first lug 468. A first notch 470 may be formed on the first latch 464, for example on the first lug 468. The adapter 460 also includes a first axial face 472 and a first groove 473 formed between the first axial face 472 and the first lug 468. The adapter 460 may also include an adapter guide surface 474 and an adapter alignment edge 476. Further, a first radial gap 478 may be formed between an outer surface of the first inner collar 462 and an inner surface of the first latch 464. In one embodiment, the adapter 460 includes two first latches 464 which may be similarly formed.

Figure 28:
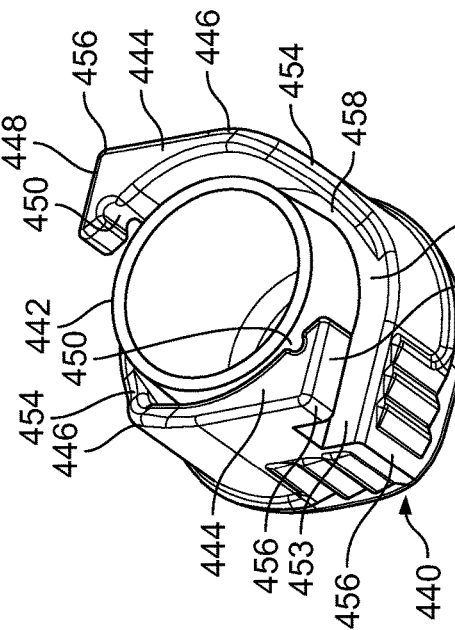
FIG. 28 is a perspective view of the closure of FIG. 18, according to an embodiment.
Figure 27:
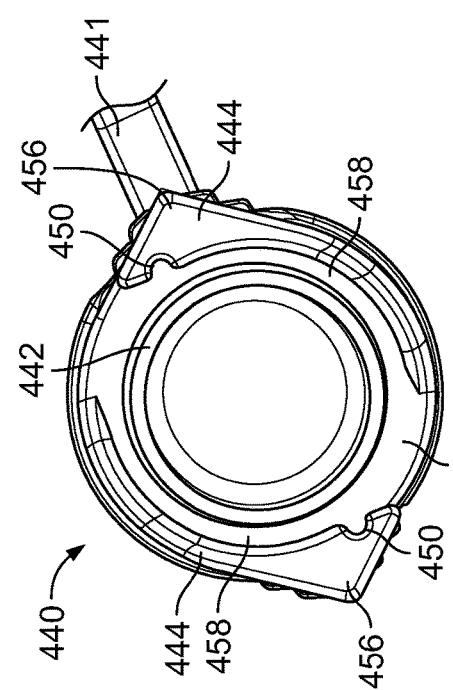
FIG. 27 is a bottom view of the closure of FIG. 18, according to an embodiment.

FIG. 27 is an enlarged bottom view of the closure 440 and FIG. 28 is a bottom perspective view of the closure 440, according to an embodiment described herein. In one embodiment, the closure 440 may be substantially identical to the adapter 460, except that the closure 440 does not include an opening through which the contents of the ostomy pouch 10 may flow. That is, the closure 440 does not have a part which corresponds to the adapter opening 461.

Accordingly, in one embodiment, and with reference to FIGS. 18, 20, 27 and 28, the closure 440 includes a second inner collar 442 and a second latch 444 having a second base 446 and a second lug 448. A second notch 450 may be formed on an inner surface of the second latch 444, for example on the second lug 448. The second lug 448 is spaced from a second axial face 452 by a second groove 453. The second latch 444 may also include a closure guide surface 454. The closure 440 may also include a closure alignment edge 456 on an exterior surface of the closure 440. The closure alignment edge 456 may be formed substantially the same as the alignment edge 436 of the outlet body 420. The second inner collar 442 and the second latch 444 are spaced apart by a second radial gap 458. In one embodiment, a portion of the outlet body 420 may be received in the second radial gap 458 when the closure 440 is coupled to the outlet body.

In one embodiment, the second inner collar 442, the second latch 444, the second base 446, the second lug 448, the second notch 450, the second axial face 452, the second groove 453, the closure guide surface 454, the closure alignment edge 456 and the second radial gap 458 of the closure 440 correspond, respectively, to the first inner collar 462, the first latch 464, the first base 466, the first lug 468, the first notch 470, the first axial face 472, the first groove 473, the adapter guide surface 474, the adapter alignment edge 476 and the first radial gap 478 of the adapter 460. That is, the parts of the closure 440 described above may be formed having substantially the same size, shape and relative positioning, for example, as the corresponding parts on the adapter 460. Accordingly, the adapter 460 and the closure 440 may be interchangeably coupled to the outlet body by engagement of the first latch 464 or second latch 444 to the catch 424.

FIGS. 29-37 show different views of the adapter 460 coupled to the outlet body 420 according to an embodiment. Referring generally to FIGS. 29-37, the adapter 460 may be coupled to the outlet body 420 by moving the first latch 464 into engagement with the catch 424. For example, the latch 464 may be moved into a friction or interference fit engagement with the catch 424, and also form a mechanical interlock to restrict axial movement of the adapter 460 relative to the outlet body 420.

In one embodiment, the adapter 460 may be moved toward the outlet body 420, in the axial direction D1 for example, to position the first base 466 in the first portion 428 of the catch 424. The respective guide surfaces 434, 474 may be moved into contact with another, and such contact may cause rotation of the adapter 460 relative to the outlet body 420. Alternatively, the user may manually rotate the adapter 460 relative to the out body 420.

Movement of the adapter 460 toward the outlet body 420 positions the first inner collar 462 is in the outlet opening 422. In addition, the first lug 468 is clear of the arm 432 and moved past the arm 432. Rotation of the adapter 460, referred to above, causes first lug 468 to move into the second portion 430 of the catch 424. The first notch 470 is configured to engage the protrusion 436 in a friction or interference fit. In addition, the arm 432 is received in the first groove 473 to form the mechanical interlock. The adapter 460 may be coupled to the outlet body 420 in the first condition.

The adapter 460 may be removed from the outlet body 420 by rotating the adapter 460 relative to the outlet body 420, or vice versa, to disengage the first notch 470 from the protrusion 436. Accordingly, the first lug 468 may be moved out of the second portion 430 and out of the mechanical interlock with the arm 432. The adapter 460 may then be moved away from the outlet body 420, for example in the axial direction D1, and the first collar 462 may be removed from the outlet opening 422.

In the embodiments above, an audible, tactile and/or visual feedback may be provided to the user to confirm coupling of the adapter 460 to the outlet body 420 by way of engagement of the first latch 464 and the catch 424. For example, in one embodiment, the first notch 470 and the protrusion 436 may be brought into a friction or interference fit to provide an audible or tactile "click," "pop," or the like which may be heard or felt by the user. Visual feedback and confirmation may be provided by aligning of the alignment edge 438 and the adapter alignment edge 476. Conversely, similar feedback may be provided to the user when removing the adapter 460 from the outlet body 420, in response to disengagement of the first notch 470 from the protrusion 436, and respective alignment edges 438, 476 being moved out of alignment with one another.

In one embodiment, the closure 440 may be coupled, interchangeably with the adapter 460, to the outlet body 420, by way of engagement between the second latch 444 and the catch 424. As detailed above, the closure 440 is formed similarly to the adapter 460, except that the closure is closed (i.e., does not have an opening extending therethrough) to prevent or limit egress of the contents from the pouch through the outlet opening 422. Accordingly, the closure 440 may be coupled to the outlet body 420 in substantially the same manner as the adapter 460 described above.

For example, in one embodiment, the closure 440 is moved toward the outlet body 420 to position the second inner collar 442 in the outlet opening 422 and the second base 446 in the first portion 428 of the catch 424. The closure 440 may be rotated, for example, by way of continued movement toward the outlet body 420 and contact between the respective guide surfaces 434, 454, or by manual rotation. Rotation of the closure 440 moves the second lug 448 into the second portion 430 of the catch 424. The second notch 450 may engage the protrusion 436 in a friction or interference fit and provide audible and/or tactile feedback in response to such engagement. The second lug 448 also forms a mechanical interlock with the arm 432 received in the second groove 453 to restrict movement of the closure 440 away from the outlet body 420 when coupled to the outlet body 420. Visual confirmation of coupling between the closure 440 and the outlet body 420 may be provided by alignment of the respective alignment edges 438, 456 on the outlet body 420 and the closure 440, respectively.

Figure 35:
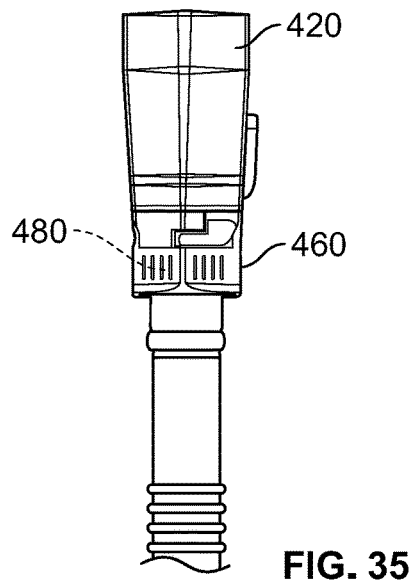
FIG. 35 is a transparent side view of the assembly of FIG. 29.
Figure 36:
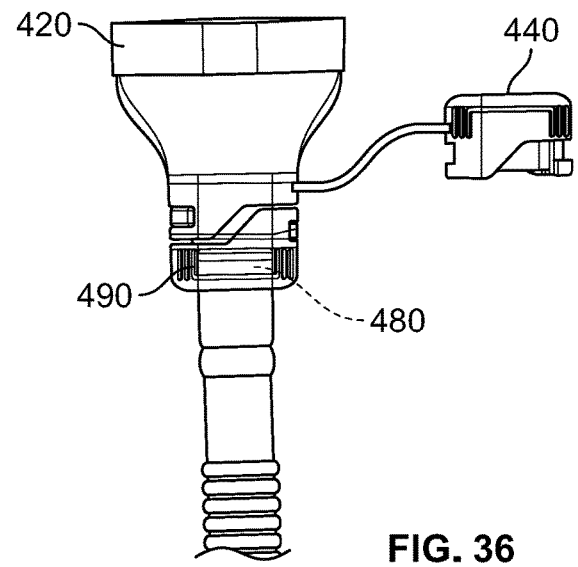
FIG. 36 is a transparent front view of the assembly of FIG. 29.

Referring to the transparent views shown in FIGS. 35 and 36, the drainage tube 480 may be coupled to the adapter 460 to connect the ostomy pouch 10, outlet body 420 and adapter 460 to a high-volume collection pouch, such as a night drainage bag (not shown). The tube 480 may be connected to the adapter 460, for example, by friction fit, heat sealing, adhesive, a mechanical fastener, combinations thereof or other suitable techniques.

Figure 37:
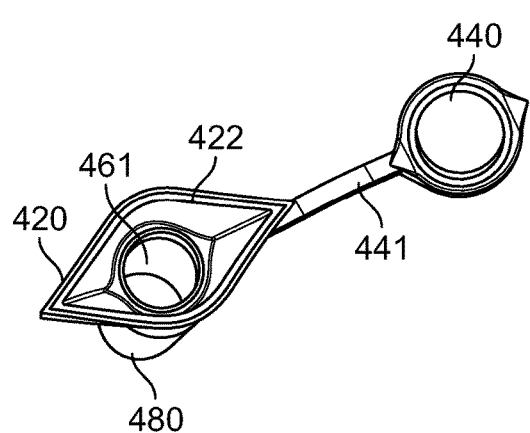
FIG. 37 is a top perspective view of the assembly of FIG. 29.
Figure 38:
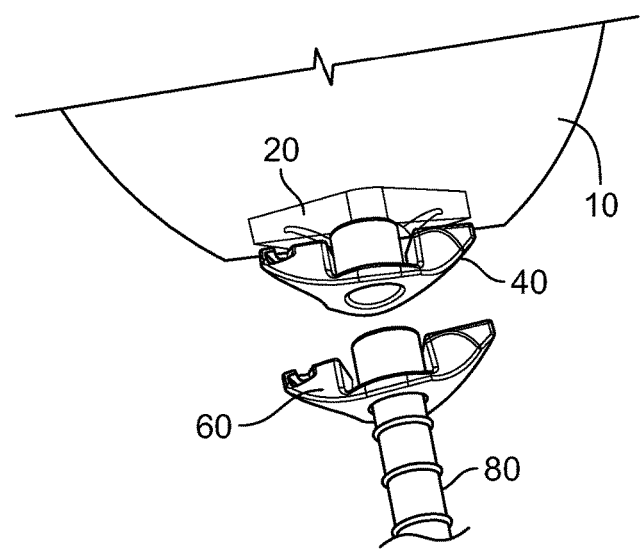
FIG. 38 is another perspective view showing the ostomy collection and drainage system of FIG. 1.

FIG. 37 is a top perspective view of the outlet body 420 coupled to drainage tube 480 via the adapter 460. As shown in FIG. 37, the outlet opening 422 is disposed in communication with the adapter opening 461 and the drainage tube 480 to allow for flow of the contents from the ostomy pouch 10 through the outlet body 420, adapter 460 and drainage tube 480, for example, to a high-volume collection pouch.

Referring again to FIG. 1, the closure 40 is removably coupled to the outlet body 20 to selectively open and close the outlet body 20, and in turn, the ostomy pouch 10. With the closure 40 coupled to the outlet body 20 (i.e., the second condition) the outlet body 20 and ostomy pouch 10 are in a closed condition such that the ostomy pouch 10 may collect and store stoma discharge as contents within the internal collection area, and unintended egress of the contents is substantially prevented or limited by way of the closure 40. The closure 40 may be removed from the outlet body 20 to allow for emptying or drainage of the ostomy pouch 10 through an outlet body 20.

The closure 40 and adapter 60 may be interchangeably coupled to outlet body 20. Thus, adapter 60 may be removably coupled to the outlet body 20 when the closure 40 is not coupled to the outlet body 20. The adapter 60 may be connected to the drainage tube 80 to allow for drainage of the contents of the ostomy pouch 10 through the outlet body 20, adapter 60 and drainage tube 80 to, for example, a high-volume collection pouch, such as a night drainage bag.

Figure 39:
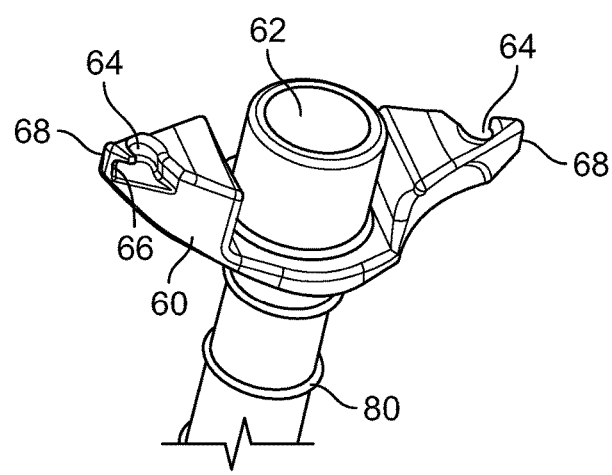
FIG. 39 is a perspective view of the adapter of FIG. 1.

FIGS. 38-44 further illustrate the outlet body 20, closure 40, adapter 60 and drainage tube 80 shown in FIG. 1. FIG. 39 is a perspective view of the adapter 60. The adapter 60 may include an adapter opening 62 and a first latch 64. In one embodiment, the first latch 64 is generally formed as a recess having a first shoulder 68 therein. The recess may be open at a top surface of the adapter 60 and a second surface, adjacent to the top surface and extending at an angle relative to the top surface so as to intersect a direction of rotation of the adapter 60 when coupling the adapter 60 to the outlet body 20. The adapter 60 also includes an adapter alignment edge 68.

Figure 40:
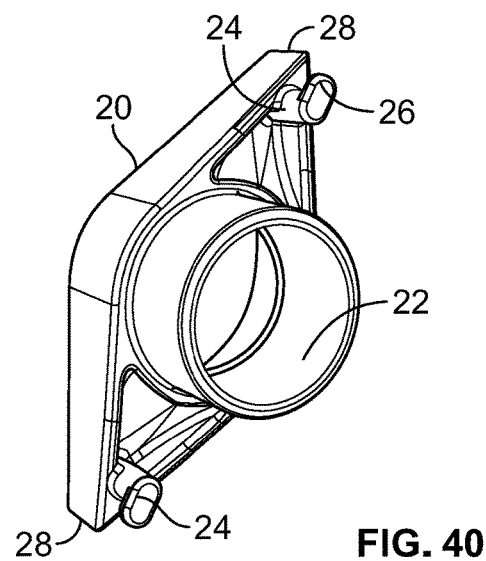
FIG. 40 is a bottom perspective view of the outlet body of FIG. 1.

FIG. 40 is a perspective view of the outlet body 20, according to an embodiment. The outlet body 20 includes, for example, an outlet opening 22, through which the contents of the ostomy pouch 10 may be drained. The outlet body 20 also includes a catch 24. In one embodiment, the outlet body 20 may include two catches 24. The catch 24 may have a foot 26 at a free end thereof. The outlet body 20 also includes an alignment edge 28.

Figure 41:
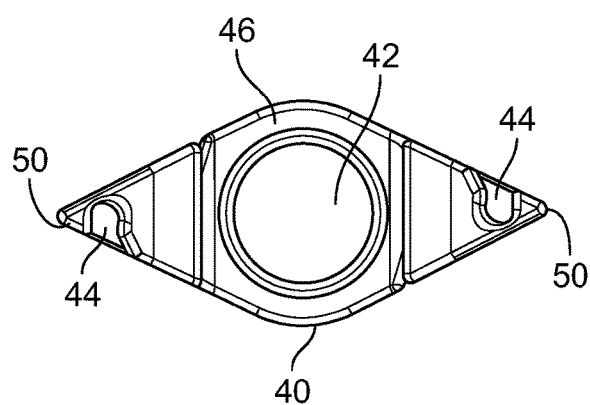
FIG. 41 is a top view of the closure of FIG. 1.

FIG. 41 is a top view of the closure 40, according to an embodiment. The closure 40 may be formed substantially the same as the adapter 60, except that the closure 40 is formed with a plug 42 and cap 46 instead of an adapter opening 62 extending therethrough. Accordingly, the closure 40 may be coupled to the outlet body 20 to substantially prevent or limit egress of the contents from the ostomy pouch 10 through the outlet body 20. In one embodiment, the closure 40 includes a second latch 44 formed as a recess having a second shoulder 48. The closure 40 may also include a closure alignment edge 50. In one embodiment, the closure 40 includes two second latches 44. In one embodiment, the second latch 44 and shoulder 48 may be configured substantially the same as the first latch 64 and first shoulder 66, respectively. In one embodiment, the plug 42 is configured to frictionally engage the outlet body 20 within the outlet opening 22. Preferably, the frictional engagement between the plug 42 and the outlet body 20 is a sealing engagement.

In one embodiment, the second latch 44 and the second shoulder 48 may be formed having substantially the same, or the same size, shape and relative position on the closure 40 as the first latch 64 and the first shoulder 66 on the adapter 60. Accordingly, the closure 40 is configured for removable coupling to the outlet body 20 in substantially the same manner as the adapter 60, as described further below.

Figure 42:
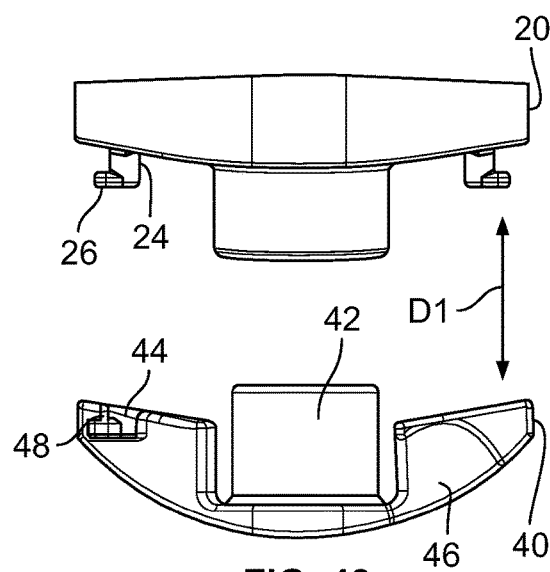
FIG. 42 is an exploded view of the outlet body and closure of FIG. 1.
Figure 43:
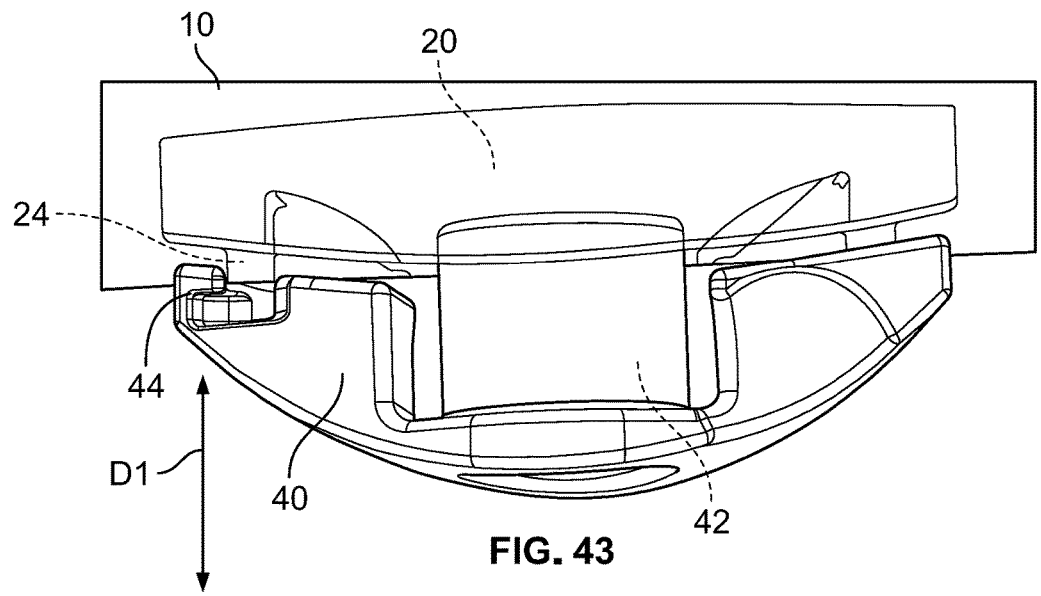
FIG. 43 is a perspective view of the closure coupled to the outlet body in the ostomy collection and drainage system of FIG. 1.
Figure 44:
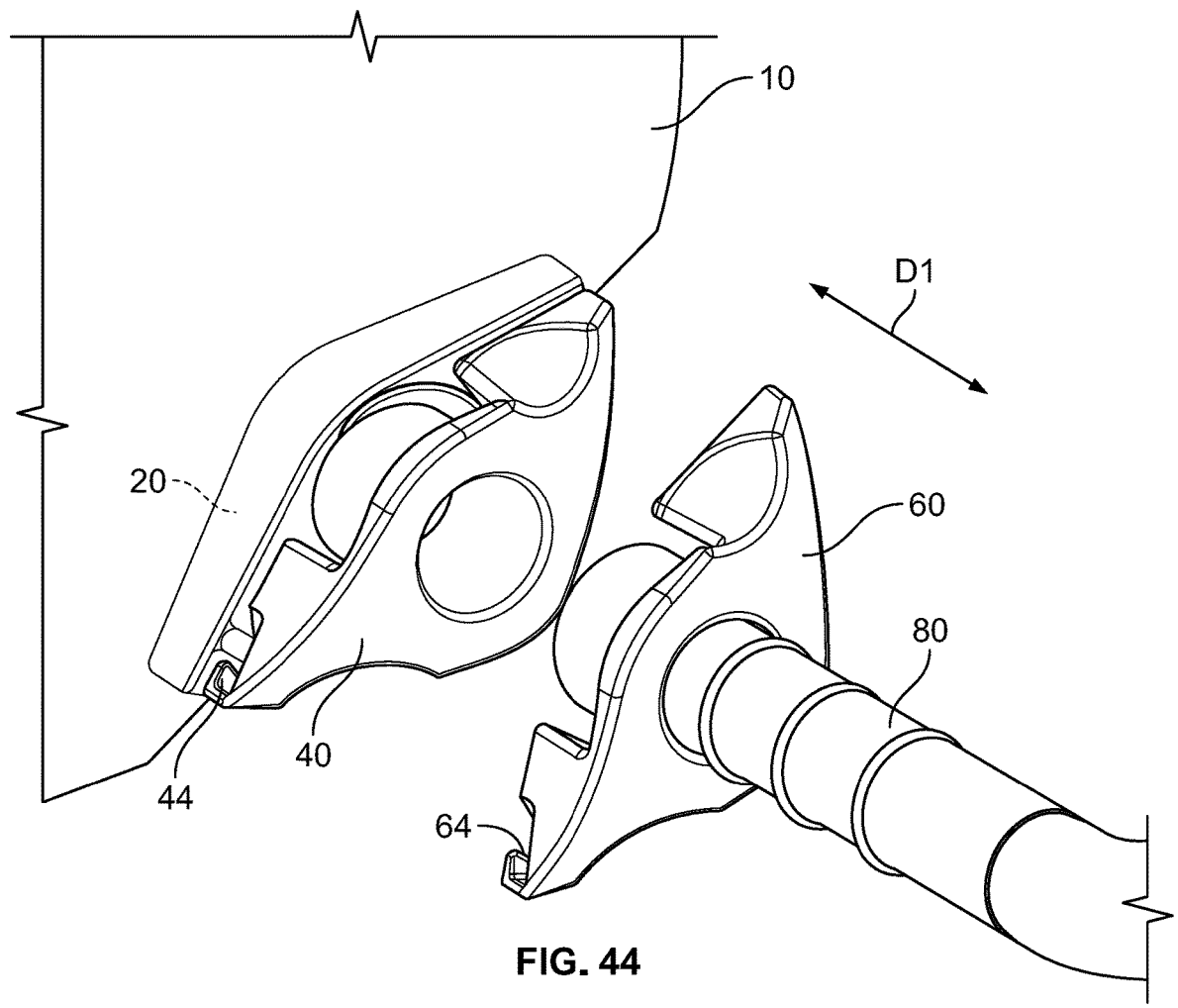
FIG. 44 is another perspective view of the ostomy collection and drainage system of FIG. 1.

FIG. 42 is an exploded view of the closure 40 and the outlet body 20 of FIG. 1, and FIG. 43 shows the closure 40 coupled to the outlet body 20. Referring to FIGS. 42 and 43, to couple the closure 40 to the outlet body 20, the second latch 44 is held at a position rotationally offset from the catch 24 with the plug 42 generally aligned with the outlet opening 22. The closure 40 may then be moved toward the outlet body 20, or vice versa, for example in the axial direction D1, such that the plug 42 is received in the outlet opening 22. The closure 40 may be rotated relative to the outlet body 20 to move the second latch 44 into engagement with the catch 24. In one embodiment, the second latch 44 and the catch 24 engage one another. For example, the second shoulder 48 may engage the foot 26 in a friction or interference fit. The foot 26 and shoulder 48 may be sized and shaped such that an audible and/or tactile "click," "pop" or the like may be provided when the closure 40 is coupled to the outlet body 20 in response to the engagement of the second latch 44 and the catch 24.

Further, in one embodiment, visual confirmation of coupling may be provided by alignment of the alignment edge 28 of the outlet body 20 and the closure alignment edge 50 of the closure 40.

To remove the closure 40 from the outlet body 20, the closure 40 may be rotated in an opposite direction to that above, such that the second latch 44 is moved outward from the catch 24. Disengagement of the second latch 44 from the catch 24, for example, disengagement of the second shoulder 48 and foot 26, may provide an audible and/or tactile "click," "pop" or the like. In addition, the rotation may move the alignment edge 28 out of alignment with the closure alignment edge 50, thereby providing visual confirmation that the closure 40 is no longer coupled to the outlet body 20. The closure 40 may then be moved away from the outlet body 20, for example in the axial direction D1, to remove the plug 42 from the outlet opening 22.

FIG. 43 is a perspective view showing the adapter 60 and drainage tube 80 positioned relative to the outlet body 20, with the closure 40 coupled to the outlet body. The closure 40 may be removed from the outlet body 20 in the manner discussed above. The adapter 60 may then be coupled to the outlet body 20.

Accordingly, in the embodiments above, a frictional engagement or interference fit between the latch or the second latch and the catch allows for additional security and retention when the adapter or closure is coupled to the outlet body. For example, the adapter or the closure may have increased resistance to rotation out of a coupled condition due to the engagement of that latch or the second latch and the catch. In addition, the engagement of the latch or the second latch and the catch may form a mechanical interlock which resists movement of the adapter or the closure away from the outlet body, for example, in a substantially axial direction. Thus, the closure and adapter may be less susceptible to inadvertent removal from outlet body.

In addition, engagement of the latch or the second latch and the tab may provide audible and/or tactile feedback to the user to confirm that the adapter or closure is properly coupled to the outlet body, such that the adapter or closure is less susceptible to inadvertent removal from the outlet body. Conversely, audible and/or tactile feedback may be provided to the user when the latch or the second latch and the tab become disengaged. Further, the outlet body, the adapter and/or the closure may include external structural features which are moved into alignment with one another when the adapter or closure are properly coupled to the outlet body, thereby providing visual feedback of proper coupling. Conversely, the structural features may be moved out of align member when the adapter or closure is moved from the proper coupling position.

Although only referred to and discussed with reference to the embodiments shown in FIGS. 2 and 20, it is understood that the outlet opening of the various embodiments above may have a width or diameter W of 15 mm-25 mm. For example, in one embodiment, the outlet opening may have a width or diameter W of 16 mm-19 mm.

Figure 45:
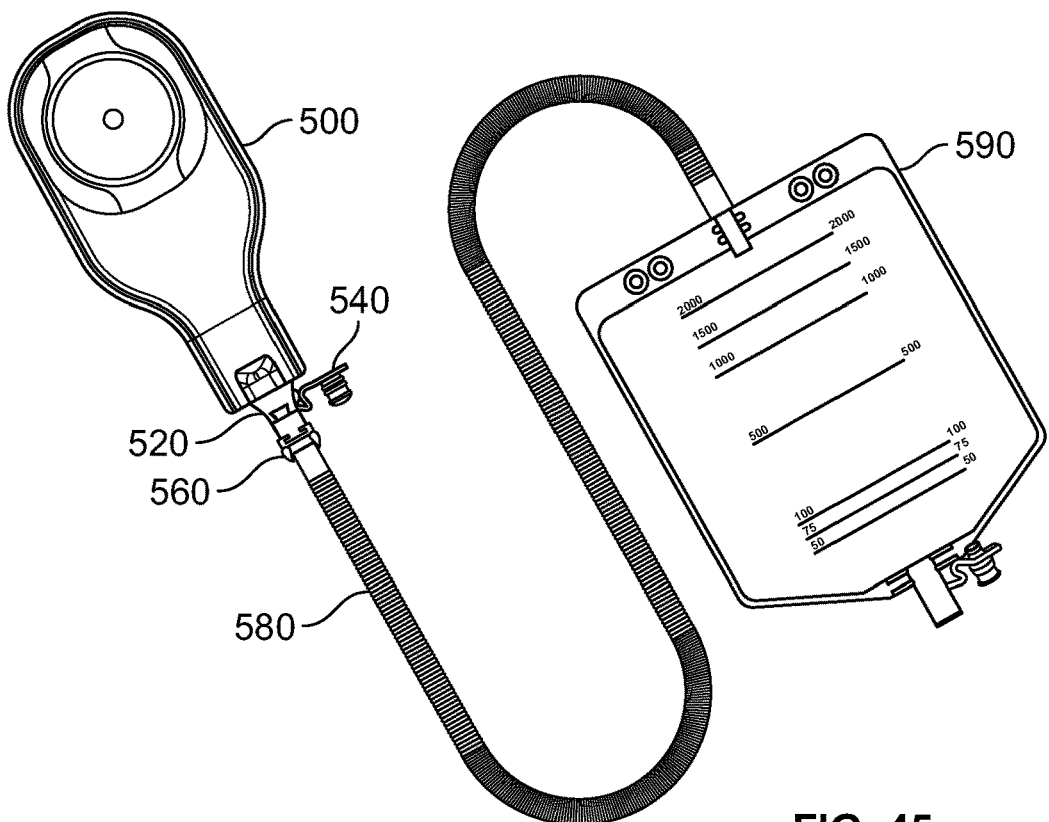
FIG. 45 is a perspective view of an ostomy collection and drainage system including an outlet body and an adapter according to an embodiment.
Figure 46:
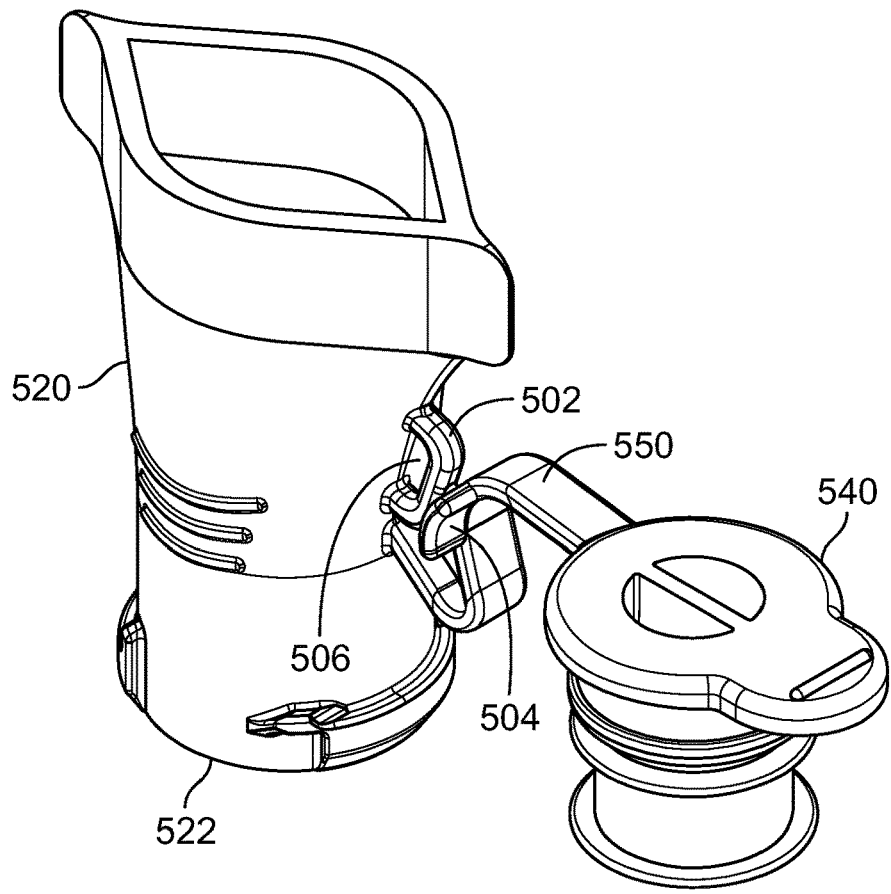
FIG. 46 is a perspective view of an outlet body including a closure docking system according to an embodiment.

Referring to FIGS. 45-50, an outlet body 520 with a closure 540 tethered thereto according to an embodiment is shown. FIG. 45 is a perspective view showing the outlet body 520 attached to an ostomy pouch 500 and an adapter 560 coupled to the outlet body 520. The ostomy pouch 500 is connected to a night drainage bag 590 via a drainage tube 580, which is attached to the adapter 560 at one end and to the night drainage bag 590 at the other end. The outlet body 520 and the adapter 560 may be formed substantially the same as the outlet body 120 and the adapter 160 described above. Accordingly, further description of like parts of the outlet body 520 and the outlet body 120 and like parts of the adapter 560 and the adapter 160 may be omitted below.

In this embodiment, the outlet body 520 may include a docking system configured to hold the closure 540 in place when the closure 540 is not engaged in an outlet opening 522 of the outlet body 520. The docking system may be configured to dock the closure 540 at a fixed place away from the outlet opening 522, such that the closure 540 does not interfere with draining of body waste collected in the ostomy pouch 500 through the outlet opening 522.

FIGS. 46-49 are various views of the outlet body 520 comprising the docking system including a first docking part 502 and a second docking part 504 according to an embodiment. In this embodiment, the first docking part 502 may be provided on the outlet body 520. The first docking part 502 may be formed as a handle like projection, which extends generally radially outward from the outlet body 520 to provide an opening 506 for receiving the second docking part 504. The second docking part 504 may be provided on a flexible member 550, which connects the closure 540 to the outlet body 520. The second docking part 504 may be configured as a tab like projection extending from a side surface of the flexible member 550. To dock the closure 540, a user may grab the closure 540 and manipulate the flexible member 550 to insert the second docking part 504 into the opening 506 defined in the first docking part 502. The first and second docking parts 502, 504 may be configured to fixedly hold the closure 540 away from the outlet opening 522.

In other embodiments, the first and second parts of the docking system may be provided in various different forms, wherein the first and second docking parts are configured to engage with each other to dock the closure 540 proximate the outlet body 520 away from the outlet opening 522. For example, the first and second docking parts may be provided as hook and loop fasteners, latch and catch, or other known mechanical or adhesive coupling systems.

Any patents referred to herein, are hereby incorporated herein in their entirety, by reference, whether or not specifically indicated as such within the text of this disclosure. Various features of the embodiments above may be used together with or replace other features of different embodiments above.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy collection and drainage system comprising:
   an ostomy pouch having an outer wall defining an internal collection area;
   an inlet opening formed in the outer wall in fluid communication with the internal collection area;
   an outlet body connected to the outer wall and having an outlet opening extending therethrough in fluid communication with the internal collection area, the outlet body having one of a latch and a catch;
   a closure configured for removable coupling to the outlet body; and
   an adapter configured for removable coupling to the outlet body, the adapter having an adapter opening extending therethrough and the other of the latch and the catch, wherein the catch and the latch are engaged in a rotational direction in an interference fit and form a mechanical interlock to restrict movement in an axial direction of the adapter relative to the outlet body;

wherein the adapter and the closure are interchangeably coupled to the outlet body such that in a first condition the adapter is coupled to the outlet body by way of engagement of the catch and the latch, and in a second condition the closure is coupled to the outlet body.

2. The ostomy collection and drainage system of claim 1, wherein the closure further comprises a second of the catch or latch that is formed on the adapter.

3. The ostomy collection and drainage of system of claim 1, wherein the outlet body comprises the catch and the adapter comprises the latch.

4. The ostomy collection and drainage system of claim 3, wherein:
- the catch projects radially outward, extends in a peripheral direction along a periphery of the outlet body, and includes a first surface, and
- the latch extends in an axial direction and includes an inwardly extending projection at a free end that is configured to engage the first surface to form a mechanical interlock and restrict movement in an axial direction of the adapter relative to the outlet body.

5. The ostomy collection and drainage system of claim 4, wherein the first surface comprises two peaks spaced from one another in the peripheral direction, the inwardly extending projection is configured for interfering movement over the peaks for positioning between the two peaks in the first condition.

\* \* \* \* \*